United States Patent
Goldberg et al.

(10) Patent No.: US 12,068,062 B2
(45) Date of Patent: *Aug. 20, 2024

(54) CUSTOMER HEALTH ACTIVITY BASED SYSTEM FOR SECURE COMMUNICATION AND PRESENTATION OF HEALTH INFORMATION

(71) Applicant: CVS Pharmacy, Inc., Woonsocket, RI (US)

(72) Inventors: Kenneth D. Goldberg, Bellingham, WA (US); Dharmendra Gudimetla, Fountain Hills, AZ (US); John A. Guido, West Warwick, RI (US); Karukamaliyil L. Sibin, Allen, TX (US); William J. Tenenbaum-Maya, Cumberland, RI (US); Alan D. Weiner, New Bloomfield, PA (US)

(73) Assignee: CVS Pharmacy, Inc., Woonsocket, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/458,524

(22) Filed: Aug. 30, 2023

(65) Prior Publication Data
US 2023/0410965 A1    Dec. 21, 2023

Related U.S. Application Data

(63) Continuation of application No. 16/785,157, filed on Feb. 7, 2020, now Pat. No. 11,862,306.

(51) Int. Cl.
*G16H 10/60* (2018.01)
*A61B 5/00* (2006.01)
(Continued)

(52) U.S. Cl.
CPC .......... *G16H 10/60* (2018.01); *A61B 5/0022* (2013.01); *A61B 5/7435* (2013.01);
(Continued)

(58) Field of Classification Search
CPC .... G06Q 20/36; A61B 5/0022; A61B 5/7435; G06F 21/6245; H04L 2209/38
See application file for complete search history.

(56) References Cited

U.S. PATENT DOCUMENTS

2002/0097277 A1    7/2002  Pitroda
2002/0169637 A1    11/2002 Akers et al.
(Continued)

FOREIGN PATENT DOCUMENTS

AU    2016101183 A4 *    9/2016
AU    2016101183 A4      9/2016
(Continued)

OTHER PUBLICATIONS

Girase, R. (2018). Personal data vault management system and secured data access to service provider using blockchain technology (Order No. 10836925). Available from ProQuest Dissertations and Theses Professional. (2050554654). (Year: 2018).*
(Continued)

*Primary Examiner* — Jason S Tiedeman
*Assistant Examiner* — Emily Huynh
(74) *Attorney, Agent, or Firm* — Patent Law Works LLP

(57) ABSTRACT

A system and method for identifying health data associated with a health activity and processing the health data based on protected health information control for secure viewing and communication are provided. The method includes: detecting, by one or more processors, a health activity from a hardware device accessed by a user; identifying, by the one or more processors, health data associated with the health activity; identifying, by the one or more processors, a task to
(Continued)

be performed based on the health activity; determining, by the one or more processors, whether the user is an authorized user based on a protected health information control unit; and responsive to the user being authorized, performing the task using the health data for the authorized user.

18 Claims, 23 Drawing Sheets

(51) Int. Cl.
  *G06F 21/62* (2013.01)
  *G16H 15/00* (2018.01)
  *G16H 80/00* (2018.01)
  *H04L 9/06* (2006.01)
  *H04L 9/00* (2022.01)

(52) U.S. Cl.
  CPC ......... *G06F 21/6245* (2013.01); *G16H 15/00* (2018.01); *G16H 80/00* (2018.01); *H04L 9/0637* (2013.01); *H04L 9/50* (2022.05)

(56) References Cited

U.S. PATENT DOCUMENTS

| | | |
|---|---|---|
| 2003/0069266 A1 | 4/2003 | Wang et al. |
| 2006/0235031 A1 | 10/2006 | Arnold et al. |
| 2007/0180140 A1 | 8/2007 | Welch et al. |
| 2010/0332404 A1 | 12/2010 | Valin |
| 2012/0251993 A1 | 10/2012 | Chidambaran et al. |
| 2013/0067319 A1 | 3/2013 | Olszewski et al. |
| 2013/0073336 A1 | 3/2013 | Heath |
| 2014/0032259 A1 | 1/2014 | LaFever et al. |
| 2014/0099317 A1 | 4/2014 | Suri et al. |
| 2016/0117472 A1 | 4/2016 | Padmani et al. |
| 2016/0199487 A1 | 7/2016 | Gu et al. |
| 2016/0371444 A1 | 12/2016 | Fidone |
| 2017/0076109 A1 | 3/2017 | Kaditz et al. |
| 2017/0109475 A1 | 4/2017 | Kaditz et al. |
| 2017/0109570 A1 | 4/2017 | Finkelstein et al. |
| 2017/0124107 A1 | 5/2017 | Emberson |
| 2017/0300627 A1* | 10/2017 | Giordano ............ G06F 21/6245 |
| 2018/0028755 A1 | 2/2018 | Philip et al. |
| 2018/0060496 A1 | 3/2018 | Bulleit et al. |
| 2018/0137247 A1 | 5/2018 | Bore et al. |
| 2018/0211058 A1* | 7/2018 | Aunger ................ H04L 63/102 |
| 2018/0286500 A1 | 10/2018 | Guerra |
| 2018/0294047 A1* | 10/2018 | Hosseini ................ G16B 50/30 |
| 2018/0323975 A1 | 11/2018 | Curbera et al. |
| 2018/0332054 A1 | 11/2018 | Ford |
| 2019/0012466 A1 | 1/2019 | Ricotta et al. |
| 2019/0027237 A1 | 1/2019 | McFarlane |
| 2019/0108898 A1 | 4/2019 | Gulati |
| 2019/0130114 A1 | 5/2019 | Smith et al. |
| 2019/0156923 A1 | 5/2019 | Kain et al. |
| 2019/0180862 A1 | 6/2019 | Wisser et al. |
| 2019/0206519 A1 | 7/2019 | Eteminan et al. |
| 2019/0227999 A1 | 7/2019 | Simeonov |
| 2020/0005912 A1* | 1/2020 | Saliman ................ G16H 20/00 |

FOREIGN PATENT DOCUMENTS

| | | |
|---|---|---|
| CA | 2929508 A1 | 11/2017 |
| WO | 2016171542 A1 | 10/2016 |
| WO | 2018005445 A1 | 1/2018 |
| WO | 2018089843 A1 | 5/2018 |
| WO | 2018226919 A1 | 12/2018 |
| WO | 2019089044 A1 | 5/2019 |
| WO | 2019122414 A1 | 6/2019 |

OTHER PUBLICATIONS

Girase et. al., Personal Data Vault Management System And Secured Data Access To Service Provider Using Blockchain Technology, Master of Science, University of Massachusetts Lowell (2018).

* cited by examiner

Library & Tools
116

Enterprise
800

Third Party
830

Figure 8A

CUSTOMER HEALTH ACTIVITY BASED SYSTEM FOR SECURE COMMUNICATION AND PRESENTATION OF HEALTH INFORMATION

FIELD OF THE DISCLOSURE

The disclosure relates generally to the field of healthcare, and more particularly to a system and method for identifying health data associated with a health activity and processing the health data based on protected health information (PHI) control for secure viewing and communication.

BACKGROUND OF THE DISCLOSURE

As information technology evolved from the client server model to the Rich Internet Access type models, problems arose in digital health paradigms. One primary problem occurred when the customer technologies that touch the end user evolved to have more of the processing and information to perform its functionality than the backend domain (e.g., shockwave or java running in a browser). During this time, the IT paradigm companies developed communications protocols and tools for domains to communicate to other domains by abstracting each domain into Application Program Interfaces (APIs). This created a gap in innovation for companies that attempted to keep up to the latest customer technologies versions of hardware and software since these companies had to continually rework the APIs.

For example, adding a voice device to support a minimal health activity, e.g., making an appointment, may require extensive backend modifications to the APIs needed in the subdomains of an existing domain solution. Further, to support the same activity across other similar customer solutions (e.g., other smart speakers), more API modifications are required. Thus, continually modifying an API layer to add new speaker type interfaces becomes expensive, especially when it is necessary to maintain the quality to a specific standard. Moreover, using the API as the abstraction layer is also limiting on the range of how an activity can be leveraged across other customer technologies.

Another technology problem in digital health paradigms is the protected health information (PHI) control issue within and outside a domain. When there is an event causing a caregiver to be triaged, multiple domains (e.g., hospitals, nurse practices, primary care providers) with multiple actors (e.g., doctors, nurses, practitioners, emergency responders, billing, family, friends) may be triggered to react over time. The problem is how to give all the actors their authorized view of information for their context, and enable the actors to pass on the visibility to the next shift's actors.

A caregiver, who tries to be involved in all exams and all nurses' visits, may repeat the same story for months over and over to different actors (even within the same domain), but it becomes difficult during shift changes and when the caregiver is not there. Another caregiver may take movies and photos and have a website for other caregivers to go check, but there is no PHI control. Also, there is no solution that allows a caregiver to give control to a nurse to access data, where the nurse can also grant control to another nurse to access the data at a remote time without the caregiver being present. Moreover, there is no integration of augmented reality and spatial computing with PHI control.

SUMMARY

In view of the foregoing, a system and method for identifying health data associated with a health activity and processing the health data based on protected health information (PHI) control for secure viewing and communication is disclosed. In particular, the disclosed system and method is implemented by detecting, by one or more processors, a health activity from a hardware device accessed by a user; identifying, by the one or more processors, health data associated with the health activity; identifying, by the one or more processors, a task to be performed based on the health activity; determining, by the one or more processors, whether the user is an authorized user based on a protected health information control unit; and responsive to the user being authorized, performing the task using the health data for the authorized user.

The technologies of the present disclosure may be particularly advantageous for at least the following reasons. Since the present disclosure moves the abstraction of a health activity away from the server level, the disclosed solution can easily adapt to the evolution of the customer technologies. For example, when the hardware gets faster and lasts longer, uses smaller batteries, and supports a higher speed internet access without wires, the disclosed solution may react rapidly with little economic development impact while keeping the quality level as expected based on leveraging the evolving customer technologies. The present disclosure also unifies health care interactions across all health care fields by abstracting the solution for a health activity at a customer interaction layer, which avoids continual and expensive modifications to different APIs, and thus significantly increases the efficiency and saves the cost on computing power, network bandwidth, and other computer resources. Further, by using the PHI control to add the customers' relationships to the ecosystem of data, the disclosed solution is advantageous in improving the caregiving value. The relationships added to the ecosystem are intimate to the customers, which gives the customers a good reason to feel safe for the long run, and in turn provides the system more retaining power for those customers. Moreover, the disclosed solution allows the access rights to specific data to be authorized and assigned by the owner of the data to a different user, which guarantees the secure distribution of data within a group of authorized and preferred users. Also, a particular user, the delegate being authorized a certain level of access rights, can only pass on the certain or lower level of rights to another person. This improves the efficiency and security of access control while extending the access control to more users.

BRIEF DESCRIPTION OF THE DRAWINGS

FIG. 8A-8C are block diagrams of an example library & tools in accordance with the present disclosure.

DETAILED DESCRIPTION

Figure 1A:
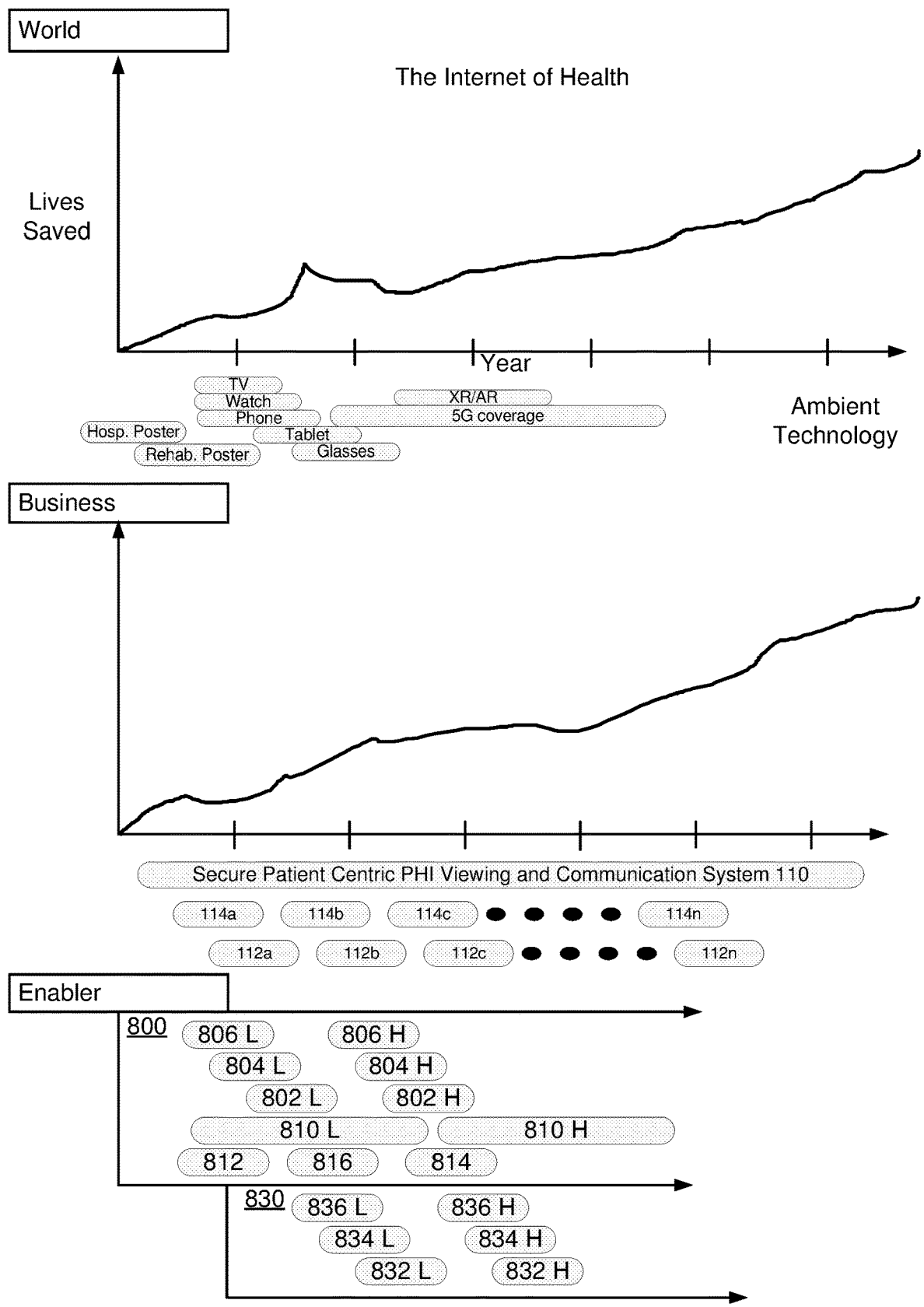
FIG. 1A shows graphic representations of the contribution and effects using a secure patient centric protected health information (PHI) viewing and communication system integrated with customer technology in accordance with the present disclosure.

Systems and methods for identifying health data associated with a health activity and processing the health data based on protected health information (PHI) control for secure viewing and communication in accordance with the present disclosure will now be described more fully with reference to the accompanying drawings.

As described above, when adding technology such as voice interaction to the existing APIs, the current system would need to continually go into the APIs and their children domains to implement the functionality. Although IT companies have started to delve into engineering solutions based on adopting agile type methodologies over the classical waterfall, there still lacks an efficient and agnostic framework to support a fruitful agile methodology. The present disclosure solves this technology issue by creating platform agnostic solutions for health activities, i.e., building a quality framework that addresses the industries paradigm from the acquisition, control, and processing perspectives.

The key of a platform agnostic solution is to move the abstraction layer of a health activity to the customer interaction layer instead of at the server level. For example, when a customer wants to know "when is a good time to go to the store?" this user interaction is taken as a health activity. The health activity encompasses all forms of user interactions from hardware devices associated with users. Therefore, if users interact with an activity on their phones by voice or their TVs using text, these interactions will be taken as a same health activity and the users will get a same result.

Another key for the platform agnostic solution provided in the present disclosure is access control to a health activity. By storing data that is used in the activity with a protected health information control unit (PHICU) to control access to that data, the present disclosure can enable the health activity to be used by other caregivers. It is worthy noting that the data stored in the PHICU is only access authorization data. This means that the health activity data still resides in the domain of choice. For example, a video of the patient is still stored on a patient's computer and the result from a doctor is still stored in a database on the doctor's side. Storing data in a local domain is advantageous in reducing the network bandwidth and computer resources that would otherwise be used to transmit the data between domains (considering an activity that is associated with data in external domains at various hospitals as well as in internal domains of a healthcare entity).

One healthcare question is who has access to certain data. For example, it needs to be controlled who can read or change value(s) of a patient's data. By processing the health data based on protected health information (PHI) control, the present disclosure allows only authorized users to get a level of control of the data. The present disclosure provides a caregiving solution where a first user (e.g., a patient) not only has his/her own control over viewing and modifying the data but he/she can give a certain level of control to a second user. The second user may then pass on his/her level or lower level of access to the PHICU data to a third user. The access control is therefore extended.

It is important to note, however, that the disclosed systems and methods may be embodied in many different forms and should not be construed as limited to the implementations set forth herein. Rather, these implementations are provided so that this disclosure will fully convey the scope of the claims. In the drawings, like numbers refer to like elements throughout.

In addition, while the present disclosure is described in the context of healthcare system, the disclosed systems and methods may also be applied to other transitions or changes to member benefits or network coverage, for example, banks, colleges, etc.

FIG. 1A are graphic representations of the contribution and effects using a secure patient centric protected health information (PHI) viewing and communication system integrated with customer/ambient technology.

The Internet of Health (IoH) is a concept that describes uniquely identifiable devices connected to the Internet and able to communicate with each other, used in the medical area. These solutions enable, for example, localization and real-time information about assets. Remote or automatic management of resources is possible too. This leads not only to higher quality care and time-saving, but also ensures patient safety. Thanks to the IoH, managing medical facilities is more efficient with uninterrupted access to equipment, data and patients' information. The most important features of most IoH solutions are flexibility and personalization. Systems can be adapted to every facility, no matter what specialization or size. They can also be integrated with existing technologies and software, connected and modified.

Due to these advantages and benefits, IoH has a fundamental effect on healthcare area. As can be seen from the top chart in FIG. 1A, the lives saved around the world due to the introduction of the technologies including IoH into healthcare have continuously increased over the years. For instance, as compared to the traditional information transmission approaches such as hospital posters, the introduction of mobile phones, tablets, and smart glasses in recent years has obviously contributed to the increase in saved lives. With the recent development in the ambient technology, such as XR/AR (extended reality/augmented reality) and 5G coverage, the benefits of IoH on healthcare will only become more prominent.

With the advancement of IoH, secure communication and presentation of health information become more and more important. The middle chart in FIG. 1A shows how business is advanced based on leveraging customer technology in a secure patient centric protected health information viewing and communication system 110 (described below in FIG. 1B) in the present disclosure. The system 110 integrates the customer or ambient technology in its components of health activity unit 112 and human interface module 114. As can be seen, with the evolution of customer technology, the business also evolves. For example, with the application of XR/AR features in the system 110, a user may get the information she/he needs in a three-dimensional view by simply waving her/his hand. Such convenient operation would easily bring more and more users of the system. These customer leveraging technologies, while driving the growth of the healthcare business in general, may also put the patients at risk because of the leak of access control. Therefore, blockchain technology using PHI is introduced to increase security.

To effectively control caregiving PHI to improve communication security, a variety of technologies, i.e., "enabler" technologies, are used to ensure secure communication and presentation of health information in the present disclosure. As shown in the bottom chart in FIG. 1A, the disclosed enabler includes two main parts 800 and 830, each including a plurality of components. A component itself may evolve as customer technologies and other technologies evolve. For example, 810L and 810H respectively represent the low-resolution version and high-resolution version of a health advocate application as technology grows. These different components work together to achieve increased security of communication of PHI. The specific functions of the enabler and each included component will be described further in detail with reference to FIGS. 8A-8C below.

Figure 1B:
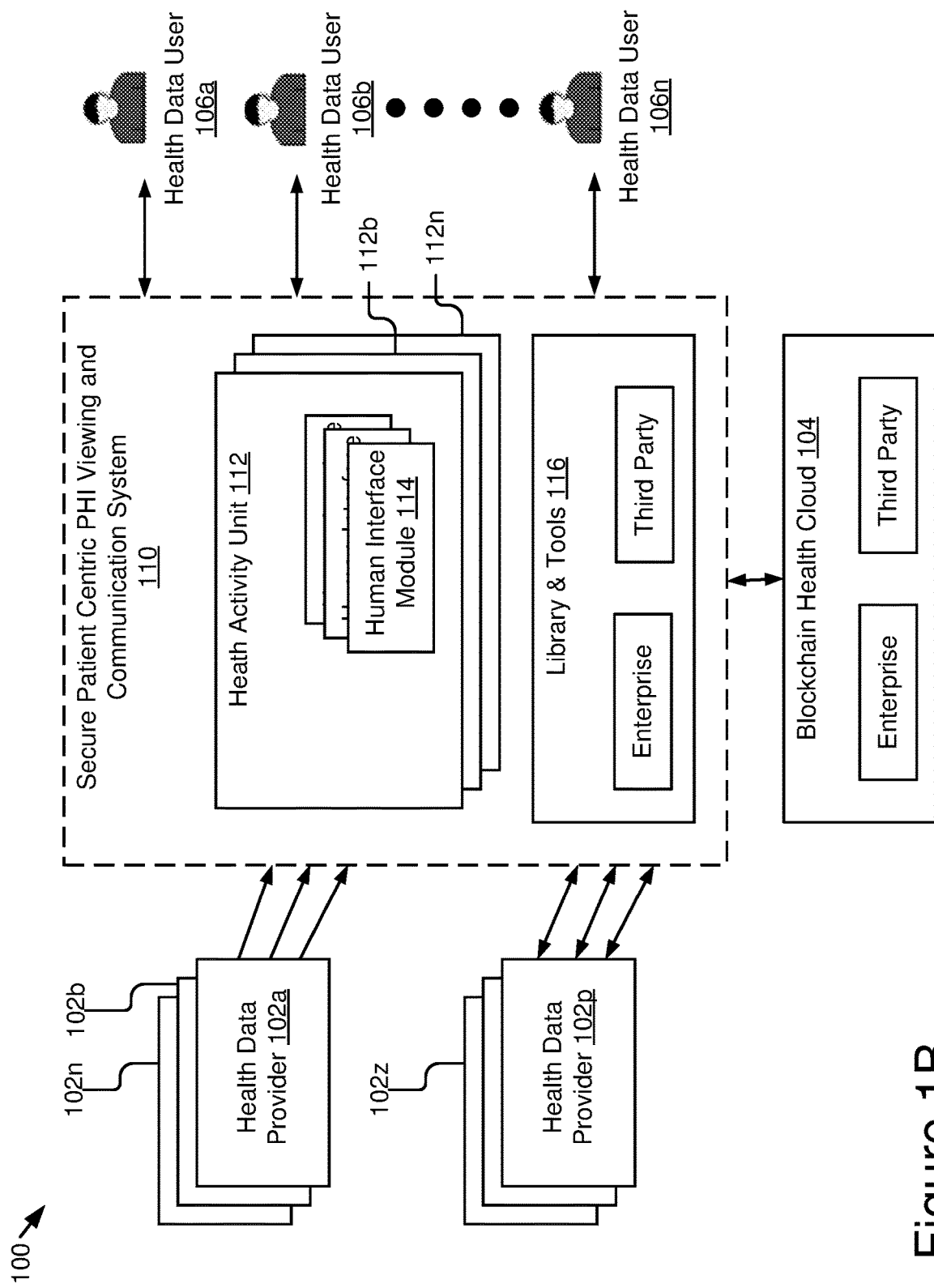
FIG. 1B is a block diagram illustrating an example health activity based system in accordance with the present disclosure.

An example customer health activity based system 100 in accordance with the present disclosure is depicted in FIG. 1B. The system 100 includes health data providers 102a . . . 102n, health data providers 102p . . . 102z, health data users 106a . . . 106n, a secure patient centric PHI viewing and communication (PHIVC) system 110, and a blockchain health cloud 104.

A health data provider may be any type of computing device associated with a healthcare entity such as a pharmacy, a hospital, a laboratory, a clinic, etc. The health data provider stores health data of patients and makes the health data available to one or more health data users. As illustrated in FIG. 1B, each of the health data providers 102a . . . 102n is a one-directional provider that connects to the PHIVC system 110 in one direction. The one-directional providers 102a . . . 102n supply the health data to the health data user 106a . . . 106n through the PHIVC system 110 responsive to receiving the health activities from the health data users. Each of the health data providers 102p . . . 102z is a bi-directional provider that connects to the PHIVC system 110 in two directions. In addition to providing the health data to the health data users 106a . . . 106n, the bi-directional provider 102p . . . 102z also receives and extracts the health data of health data users 106a . . . 106n from the PHIVC system 110 based on access authorization from the corresponding health data user.

The health data or health activity data includes data used in or related to a health activity. For example, if a patient wants to make an appointment to get a certain vaccine, the data used in this health activity may include information identifying the patient, a medical record of the patient, insurance information about the patient, information about a prescribing physician, inventory information of a pharmacy, office hours of the pharmacy, etc. The health activity may include a user interaction related to a healthcare need, which is of different types and is obtained through different types of user devices. For example, a user may interact with a health activity on a smart phone, a smart speaker, a smart glass, etc., by voice, text, hand gesture, etc.

In some implementations, the health data may include pharmacy data. The pharmacy data is information gathered or derived by a pharmacy or healthcare entity about the patients it provides prescriptions to and the medications it dispenses. For instance, any information collected during the front-of-store transactions and medication dispense by the pharmacy or healthcare entity may be recorded and stored as the pharmacy data. The pharmacy data may include pharmacy claims data about patients such as medication names, dosages, instructions for use, a number of refills, a prescribing physician's name, whether a particular prescription was picked up by the patient, a date the prescription was filled and/or picked up from the pharmacy, and so forth. The pharmacy data may also include data derived or calculated from the information about patients and the pharmacy claims data. For example, and without limitation, the pharmacy data may include a number of prescribing physicians for a patient, an adherence ratio for a patient, a medication possession ratio (MPR) of a patient, whether a patient is diagnosed with a high-risk health condition, a pharmacy risk group (PRG) assessment, and so forth.

In other implementations, the health data may also include client data. The client data includes data identifying patients, as well as data about a patient's health status, and other related information. For example, the information about a patient may include his/her names, age, address, identification number, telephone or other contact information, a name of a primary care provider, a health insurance ID number, and so forth. The client data may also include data irrelevant to the healthcare-related information. For instance, the client data for a patient may include his/her preference, habits, and any activities that may be collected by the system. For instance, a patient's online activities and his/her social network may be collected and stored in the client data.

The pharmacy data and the client data are example health data that may be obtained from health data users 106a . . . 106n through the PHIVC system 110 or from resources such as a pharmacy benefit management (PBM) program, an environment public health (EPH) program, etc. However, the health data is any data used in or related to a health activity, which includes but is not limited to pharmacy data and client data. For example, the health activity data may include the data recording the health activity itself, for example, a video capturing a patient taking his medication, an audio recording a patient asking a question, text of "patient X is asking 'how can I get a refill of medication Y' at 7:34 am on Jan. 11, 2020." The health activity data may be collected for different purposes. For example, the health activity data may include a video recording an elderly patient's walking and eating activities to create a baseline for the patient, or to be used for a certain statistical analysis related to elderly patients. There are other types of health activity data (e.g., insurance data) obtained from different resources, which will not be described in detail herein.

It is important to note that a health activity processing module 504 that is described below in FIG. 5 may identify many types of data as health data based on different criteria. One type of data may be irrelevant to a first health activity but closely related to a second health activity. For example, location data may be unrelated to a query about a kid's medical bill but is critical to a patient requesting an ambulance service. Example types of health data will be described below with reference to FIG. 14.

The health data users 106a . . . 106n or collectively referred herein as health data user 106 include patients, nurses, doctors, friends, family members, or any other users that take a health activity and access the health data used in the health activity. A health data user 106 interacts with the PHIVC system 110 via a hardware device to which the health data user 106 is accessing to exchange the health activity data with a health data provider. The hardware device will be described below with reference to FIG. 4.

In some implementations, the health data user 106 may send a request for health data (e.g., through a health activity) and receive the requested data from the health data provider 102 through the PHIVC system 110. In other implementations, the health data user 106 may input specific information regarding a health activity to the PHIVC system 110, and the PHIVC system 110 converts the input to the health data of a patient for storing by the health data providers 102p . . . 102z. In yet other implementations, the health data users 106 may communicate with each other through the PHIVC system 110, for example, about the health activities and associated data of a patient.

In some implementations, the PHIVC system 110 establishes a communication channel between health data providers and heath data users and allows the health activity data to be safely transmitted between authorized users/providers. The PHIVC system 110 may communicate with the blockchain health cloud 104 to receive an input regarding a health activity from a health data user 106, identify health data based on the input, determine whether to present the health data for view by the health data user 106 or to store the health data for a health data provider 102 to access by other health data users, and present or store the health data based on a right delegated to the health data user.

In other implementations, the PHIVC system 110 may perform analytics tasks, media tracking tasks, performance monitoring tasks, or other tasks on the acquired data. For example, the PHIVC system 110 may perform timeline control over health activity data of one or more users to generate one or more timelines to display health activities associated with the one or more users over time. The PHIVC system 110 may generate different types of notifications based on analyzing health activity data associated with a patient, identify who should receive what type(s) of notification(s) using what communication method(s), and transmit the identified notification(s) to the identified recipient(s) using the identified communication method(s). Or the PHIVC system 110 may track the online activities from social media and adjust the configuration related to a social media tool based on the tracking result to improve system performance.

The PHIVC system 110 may include one or more physical servers, virtual servers, desktop computers, or the like. In some implementations, the PHIVC system 110 incorporates one or more functional components that correspond to a sequence of instructions operative on the processing circuit (for example, one or more processors and memories) to implement logic to perform various functions as will be described in further detail hereinafter. Although the functional components are shown and described herein in a particular configuration and number, implementations may include more, fewer, or other components to provide the same or similar functionality.

As depicted, the PHIVC system 110 may include a health activity unit 112 and a library & tools 116. The health activity unit 112 may acquire, control, and process health data transmitted between health data providers and users responsive to receiving one or more health activities. For example, the health activity unit 112 may control which health data user can add or view health data of a patient. In some implementations, the health activity unit 112 includes a human interface module 114. The human interface module 114 is responsible for communicating with the health data users to receive input related to a health activity or to generate an interface for the health data users to view the health data. The operations of an implementation of the health activity unit 112 will be described below with reference to FIGS. 4 and 5.

The library & tools 116 include a collection of resources used by the health activity unit 112. For example, the library & tools 116 include configuration data, documentation, help data, message templates, pre-written code, subroutines, or type specifications that may be used by the health activity unit 112 to perform functionality such as setting preferences, querying and searching, data analyzing, etc. In some implementations, the library & tools 116 may be divided into two groups: enterprise and third-party, which respectively includes the resources corresponding to different healthcare entities in different domains. The operations of an implementation of the library & tools 116 will be explained and described below with reference to FIGS. 8A-8C.

The blockchain health cloud 104 uses the decentralization and cryptographic hashing to record the provenance of health data. The PHIVC system 110 may communicate with the blockchain health cloud 104 to determine whether a health data user can add or view the health data of a patient to or from a health data provider. Since the intent of creating the blockchain health cloud 104 is the statement of record, i.e., the final ledger, of who can access what information, the lifetime of a user (past and future information) is reserved, thereby preventing the user from diverting to other information acquisition systems.

In some implementations, the blockchain health cloud 104 may include two groups: enterprise and third-party, to contain the blocks of health data corresponding to different healthcare entities in different domains. The operations of the blockchain health cloud 104 will be explained and described below with reference to FIGS. 3, 7, and 10-13.

Other variations and/or combinations of the example system 100 are also possible and contemplated. It should be understood that the system 100 illustrated in FIG. 1B is representative of an example system and that a variety of different system environments and configurations are contemplated and are within the scope of the present disclosure. For instance, various acts and/or functionality may be moved from one server to another server or node, or vice versa, data may be consolidated into a single data store or further segmented into additional data stores, and some implementations may include additional or fewer computing devices, services, and/or networks. Further, various entities of the system may be integrated into a single computing device or system or divided into additional computing devices or systems, etc.

Figure 2A:
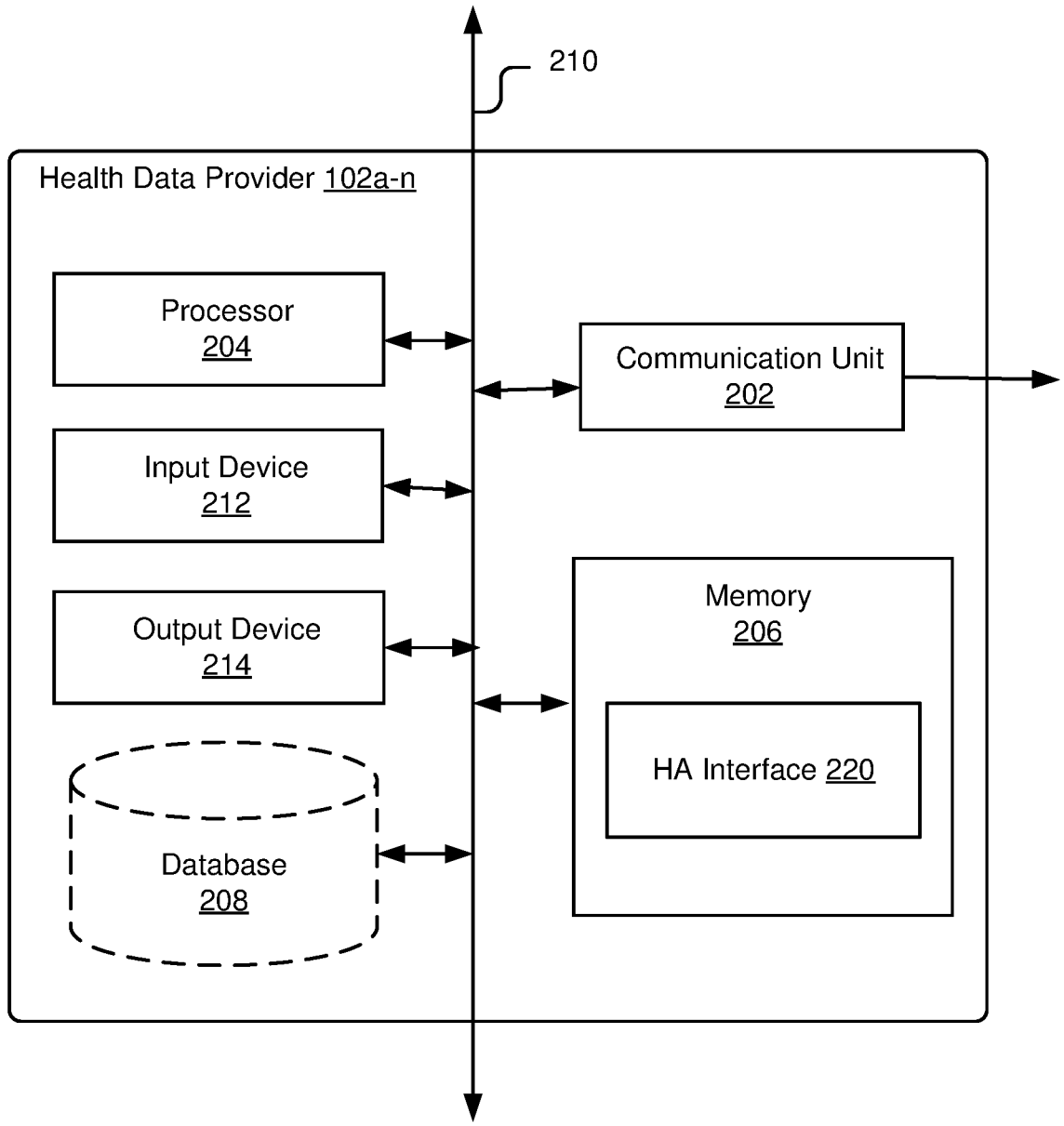
FIG. 2A is a block diagram illustrating an example unidirectional health data provider in FIG. 1B in accordance with the present disclosure.

FIG. 2A is a block diagram illustrating an example one-directional health data provider 102a . . . 102n in FIG. 1B. A health data provider 102a . . . 102n provides health data to a health data user. As depicted in FIG. 2A, the health data provider 102a . . . 102n includes a communication unit 202, a processor 204, memory 206, an input device 212, an output device 214, and a database 208, which may be communicatively coupled by a communication bus 210. The components in this figure are provided merely for illustrative purposes, but not as a limitation. More, fewer, or other components may be applicable and contemplated.

The processor 204 may be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Ltanium®, Pentium®, Xeon®, and XScale® processors; and similar processors. Dual microprocessors, multi-core processors, and other multi-processor architectures may also be employed as the processor 204.

The processor 204 may execute software instructions by performing various input/output, logical, and/or mathematical operations. The processor 204 may have various computing architectures to process data signals. In the context of the health data provider 102a . . . 102n, the processor 204 identifies the health data based on input regarding a health activity received from a health data user through a smartphone, a smart glass, etc., and retrieves the data for transmitting and displaying to the health data user. In some implementations, the processor 204 may be capable of generating and providing electronic display signals to an input/output device, supporting the display of health data, performing complex tasks including various types of data extraction, health activity state identification and modification, etc.

In some implementations, the processor 204 may be coupled to the memory 206 via the bus 210 to access data and instructions therefrom and store data therein. The bus 210 may also couple the processor 204 to the other components of the health data provider 102a . . . 102n including, for example, the input device 212, the output device 214, the communication unit 202, and database 208.

The communication unit 202 may include one or more interface devices (I/F) for wired and wireless connectivity with a network infrastructure (not shown) and the other components of the system 100. For instance, the communication unit 202 may include, but is not limited to, CAT-type interfaces; wireless transceivers for sending and receiving signals using WIFI™; Bluetooth®, cellular communications, etc.; physical interfaces (e.g., US B); various combinations thereof; etc. In some implementations, the communication unit 202 may link the processor 204 to the network infrastructure, which may, in turn, be coupled to other processing systems. The communication unit 202 may provide other connections to the network infrastructure and to other entities of the system 100 using various standard communication protocols, including, for example, those discussed elsewhere herein. In some implementations, the communication unit 202 is a set of instructions executable by the processor 204. In some implementations, the communication unit 202 is stored in the memory 206 of the health data provider 102a . . . 102n and is accessible and executable by the processor 204.

The input device 212 may include a motion-detecting input device, a pointer device, a keyboard, an audio input device, another touch-based input device, etc. The input device 212 may be managed by a physical or wireless I/O interface controller, which relays and/or passes the inputs/signals received from users via the input device 212 to one or more components of the health data provider 102a . . . 102n via the bus 210. In some implementations, an operator can enter commands and information into the health data provider 102a . . . 102n through one or more wire/wireless input device 212, for example, a keyboard and a pointing device, such as a mouse. Other input device 212 may include microphones, infra-red (IR) remote controls, radio-frequency (RF) remote controls, gamepads, stylus pens, card readers, dongles, fingerprint readers, gloves, graphics tablets, joysticks, keyboards, retina readers, touch screens (e.g., capacitive, resistive, etc.), trackballs, trackpads, sensors, styluses, and the like. This and other input devices are often connected to the processor 204 through an input device interface that is coupled to the system bus 210, but can be connected by other interfaces such as a parallel port, IEEE 1394 serial port, a game port, a USB port, an IR interface, and so forth.

The output device 214 may include a monitor or another type of display device, a speaker, a printer, etc. that is also connected to the system bus 210 via an interface, such as a video adaptor. The output device may display signals in a recognizable format to allow an indentation of information carried by the signal.

The memory 206 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. The memory 206 can include non-volatile memory and/or volatile memory. A basic input/output system (BIOS) can be stored in the non-volatile memory.

The memory 206 may store and provide access to data for the other components of the health data provider 102a . . . n. In some implementations, the memory 206 may store instructions and/or data that may be executed by the processor 204. As depicted in FIG. 2A, the memory 206 stores a health activity (HA) interface 220. When the instructions are executed, the HA interface 220 interfaces with the PHIVC system 110 for users to exchange data related to health activities. The memory 206 is also capable of storing other instructions and data, including, for example, an operating system, hardware drivers, other software applications, databases, etc.

The database 208 is configured for storing and providing access to data. The data stored by the database 208 may be organized and queried using various criteria including any type of data stored by them, such as a patient identifier, a particular preference, etc. The database 208 may include data tables, databases, or other organized collections of data. Examples of the types of data stored by the database 208 may, but are not limited to, pharmacy data, client data, data related to a health activity, etc., as discussed elsewhere herein.

The database 208 may be included in the health data provider 102a . . . 102n or in another computing system and/or storage system distinct from but coupled to or accessible by the health data provider 102a . . . 102n. The database 208 includes one or more non-transitory computer-readable media for storing the data. In some implementations, the database 208 may be incorporated with the memory 206 or may be distinct therefrom. In some implementations, the database 208 may store data associated with a database management system (DBMS) operable on the health data provider 102a . . . 102n. For example, the DBMS could include a structured query language (SQL) DBMS, a NoSQL DMBS, a file system, flat files, various combinations thereof, etc. In some instances, the DBMS may store data in multi-dimensional tables comprised of rows and columns, and manipulate, e.g., insert, query, update and/or delete, rows of data using programmatic operations.

The communication bus 210 provides an interface for system components including, but not limited to, the system memory 206 and the processor 204. The communication bus 210 can be any of several types of bus structure that may further interconnect to a memory bus (with or without a memory controller), a peripheral bus, and a local bus using any of a variety of commercially available bus architectures. Interface adapters may connect to the communication bus 210 via a slot architecture. Example slot architectures may include without limitation Accelerated Graphics Port (AGP), Card Bus, (Extended) Industry Standard Architecture ((E) ISA), Micro Channel Architecture (MCA), NuBus, Peripheral Component Interconnect (Extended) (PCI(X)), PCI Express, Personal Computer Memory Card International Association (PCMCIA), and the like.

Figure 2B:
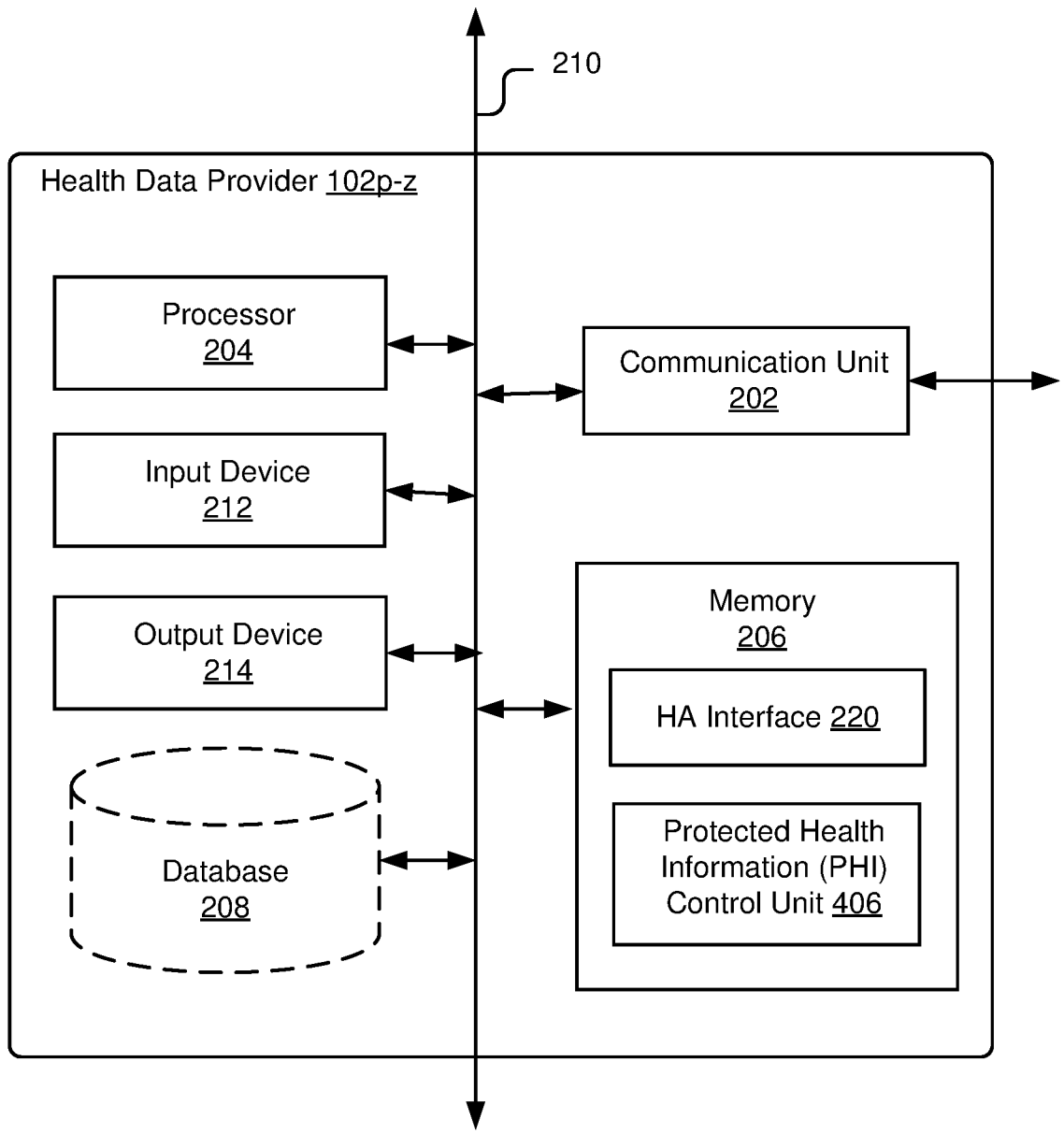
FIG. 2B is a block diagram illustrating an example bi-directional health data provider in FIG. 1B in accordance with the present disclosure.

FIG. 2B is a block diagram illustrating an example bi-directional health data provider 102p . . . 102z in FIG. 1B. In addition to providing the stored health data to a health data user, the health data provider 102p . . . 102z also extracts health data from input related to a health activity received from a health data user based on the access right authorized to the health data user. The health data provider 102p . . . 102z also includes the communication unit 202, the processor 204, memory 206, the input device 212, the output device 214, and the database 208 that are communicatively coupled by the communication bus 210 as depicted in FIG. 2A in association with the health data provider 102a . . . 102n. However, the memory 206 depicted herein in FIG. 2B stores the HA interface 220 as well as a protected health information (PHI) control unit 406. The PHI control unit 406 is used in the blockchain health cloud to determine which user can add health data and which user can view the health data. The PHI control unit 406 will be described below with reference to FIGS. 4 and 10-13.

Figure 3:
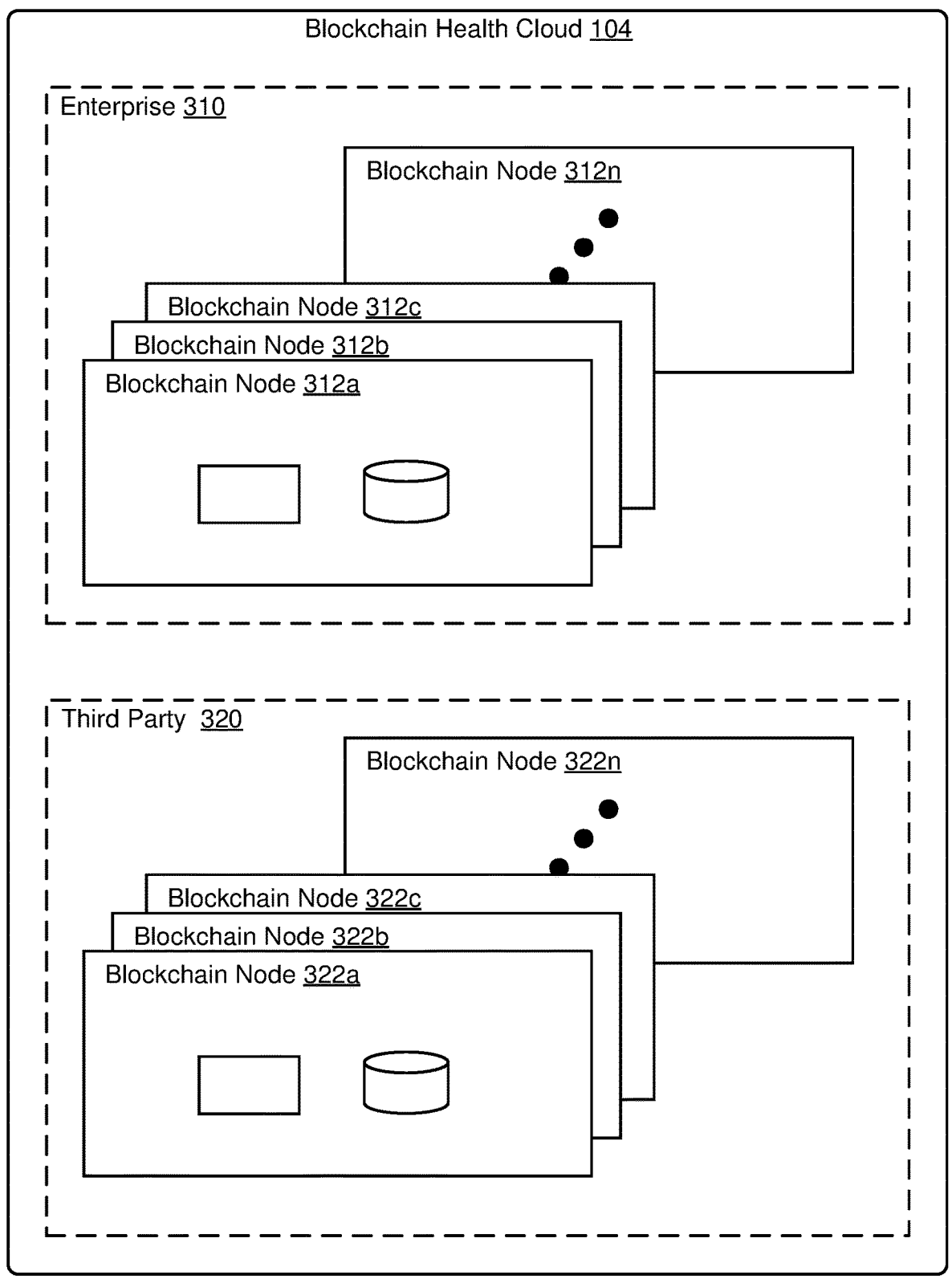
FIG. 3 is a block diagram illustrating an example blockchain health cloud of FIG. 1B in accordance with the present disclosure.

FIG. 3 is a block diagram of an example blockchain health cloud 104. The blockchain health cloud 104 is a distributed network via nodes connected to the chain and storing blocks of digital information (e.g., data related to health activities). The nodes or blockchain nodes may be any kind of electronic device that maintains copies of the blockchain and keeps the network functioning. That is the nodes, rather than a central authority, independently construct and hold data transactions. Each node runs a copy of the entire blockchain and creates a next block or validate a data transaction. Whenever a new block is added, the blockchain updates and is propagated to the entire network, such that each node is in sync.

In the example illustrated in FIG. 3, the blockchain health cloud 104 includes an enterprise cloud 310 and a third party cloud 320. The enterprise cloud 310 includes blockchain nodes such as 312a through 312n that are connected to the chain, and record and distribute the health data (e.g., data related to a health activity) on one or more internal enterprise domains (e.g., CVS® domains). The third party cloud 320 includes blockchain nodes such as 322a through 322n that are connected to the chain, and record and distribute the health data on one or more outside enterprise domains. In some implementations, the third party cloud 320 may be a separate network from the enterprise cloud 310. In other implementations, the third party cloud 320 may duplicate from the enterprise cloud 310.

As depicted in FIG. 3, each of the blockchain nodes 312 or 322 maintains the blockchain set of addresses that contain the secure health data. The secure health data may contain a smart contract to process the health data. A smart contract is computer code that is built into the blockchain to facilitate, verify, or negotiate a contract agreement. A smart contract operates under a set of conditions that users agree to. When a condition is met, a term of the agreement is automatically carried out, i.e., an action is executed. For example, when nurse A not nurse B requests for accessing a medical record of patient C, a data retrieval task is performed to provide the medical record of patient C to nurse A. Smart contracts allow the performance of credible and trackable transactions without a middleman. The working mechanism of blockchain will be described below with reference to FIGS. 7 and 10-13.

Figure 4:
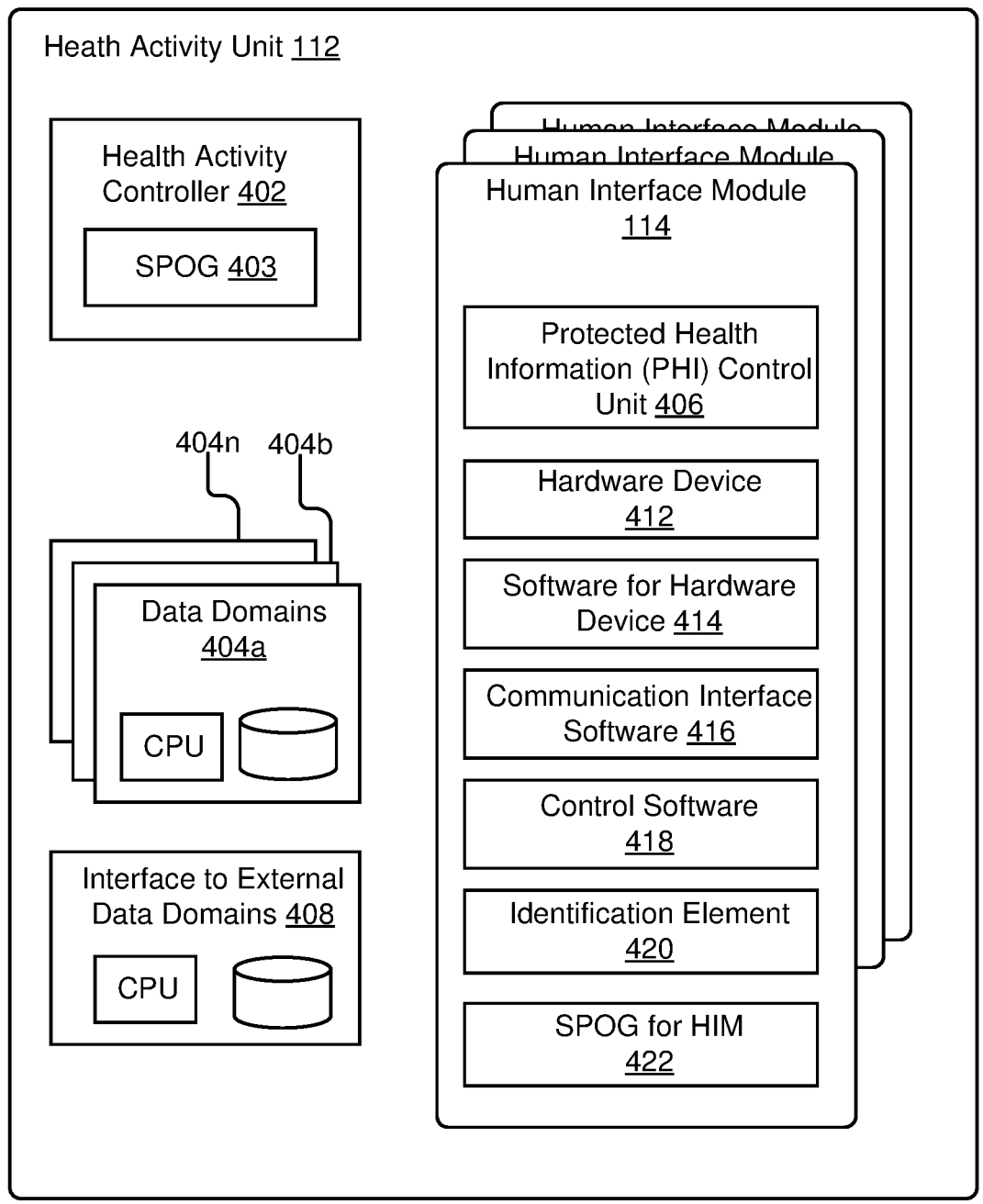
FIG. 4 is a block diagram illustrating an example health activity unit of FIG. 1B in accordance with the present disclosure.

FIG. 4 is a block diagram of an example health activity unit 112 as shown in FIG. 1B. The health activity unit 112 may acquire, control, and process health data transmitted between health data providers and users responsive to receiving one or more health activities. In the illustrated implementation, the health activity unit 112 includes a health activity controller 402, data domains 404a . . . 404n, an interface to external data domains 408, and one or more human interface modules 114. The health activity controller 402 controls the processing of health data associated with a health activity. For example, the health activity controller 402 determines which user can add the health data to a blockchain and/or which user can access the health data. In some embodiments, the health activity controller 402 may include a single pane of glass (SPOG) 403. The SPOG 403 is responsible for presenting health activity data in a unified view for the controller 402, which will be described below with reference to the SPOG for HIM 422. The SPOG for HIM 422 performs similar functions as the SPOG 403 but is associated with HIM 114. The data domains 404a . . . 404n include the internal domains of a healthcare entity. For example, the data domains 404a . . . 404n may include a patient information database, a medical record database, a prescription database, etc., that are internal to a particular health entity. The interface to external data domains 408 allows a user to interact with external data domains to retrieve the health data responsive to receiving an input regarding a health activity. For example, the data domains 404a . . . 404n represent the internal domains of CVS® Pharmacies, from which a health data user may obtain health data such as the pharmacy data. On the other hand, the interface to external data domains 408 interacts with the outside databases belonging to a hospital, a clinic or an insurance company, etc., such that the health data user may retrieve other health data from the outside databases.

A human interface module (HIM) 114 is responsible for communicating with a health data user to receive input related to a health activity or to generate an interface for the health data user to access/view the health data. Each health data user is associated with a HIM 114 to process the health activity of the user. The HIM 114 may further provide a 3D display for interacting the health data based on augmented reality features or extend reality features. A unified view not only provides more meaningful and successful interactions with users, but also makes the analysis on the health activity data more accurately, consistently, quickly, and comprehensively. In some implementations, the human interface module 114 includes a PHI control unit 406, a hardware device 412, software for hardware device 414, communication interface software 416, control software 418, an identification element 420, and a single pane of glass (SPOG) for HIM 422.

The PHI control unit 406 is a unique identification control component used in a blockchain to control access permissions of users to various data associated with a health activity, which will be further described in FIGS. 10-13.

The hardware device 412 includes any electronic device used for receiving a health activity and/or presenting the health data of the health activity. For example, the hardware device 412 is a voice speaker that is used to receive a health activity from a health data user, e.g., an audio question of "which dental clinic is closest to me?" Or the hardware device 412 is a smart glass that presents a three-dimensional (3D) interface to a health data user to view the health data relevant to multiple health incidents according to multiple timelines. In some implementations, the hardware device 412 may be a desktop, a tablet, a smart phone, a smart TV, a smart watch, a smart speaker, an automobile computer, a device supporting augmented reality (AR) and/or extended reality (XR), etc., that connects to the system through a network (not shown).

The software for hardware device 414 includes the instructions that keep the hardware device 412 functioning. For example, the software for hardware device 414 may include operating systems, device drivers, diagnostic tools, etc.

The communication interface software 416 includes the instructions that allow a user to interact with the system about the health data using the hardware device 412 associated with the user. For example, the communication interface software 416 may instruct an automobile computer to accept audio input regarding a health activity from a user.

The control software 418 implements algorithms to tell the hardware device 412 how to perform a task. The task may be related to acquiring, controlling, and processing health data. For example, the task may include identifying and retrieving health data, adding health data to a chain, determining whether to grant access control of the health data to a user, etc.

The identification element 420 identifies a specific type of hardware device used by a health data user to interact with a health activity. In some implementations, the identification element 420 may be assigned to each unique hardware device. The identification element 420 for hardware device 414 is used by the software 414, the communication interface software 416, and the control software 418 to process the health activity data associated with a wide range of hardware devices. This facilitates the abstraction of a health activity at a customer interaction layer rather than at the server level, which avoids continuous modifications to APIs, thereby saving computer resources and increasing efficiency.

The SPOG for HIM 422 generates a unified view for extending the presentation of SPOG to the health data associated with this health activity for this HIM. The view is tailored to expose the features of the associated hardware device 412 that users choose to communicate with the system to operate on the health data. Therefore, users may receive the same data for viewing when the users interact with a health activity by voice on their smart phones (e.g., when a user asked for a feature) or observe by a text stream on their smart TV (e.g., what type of shows was the user viewing when they took action on the text).

Figure 5:
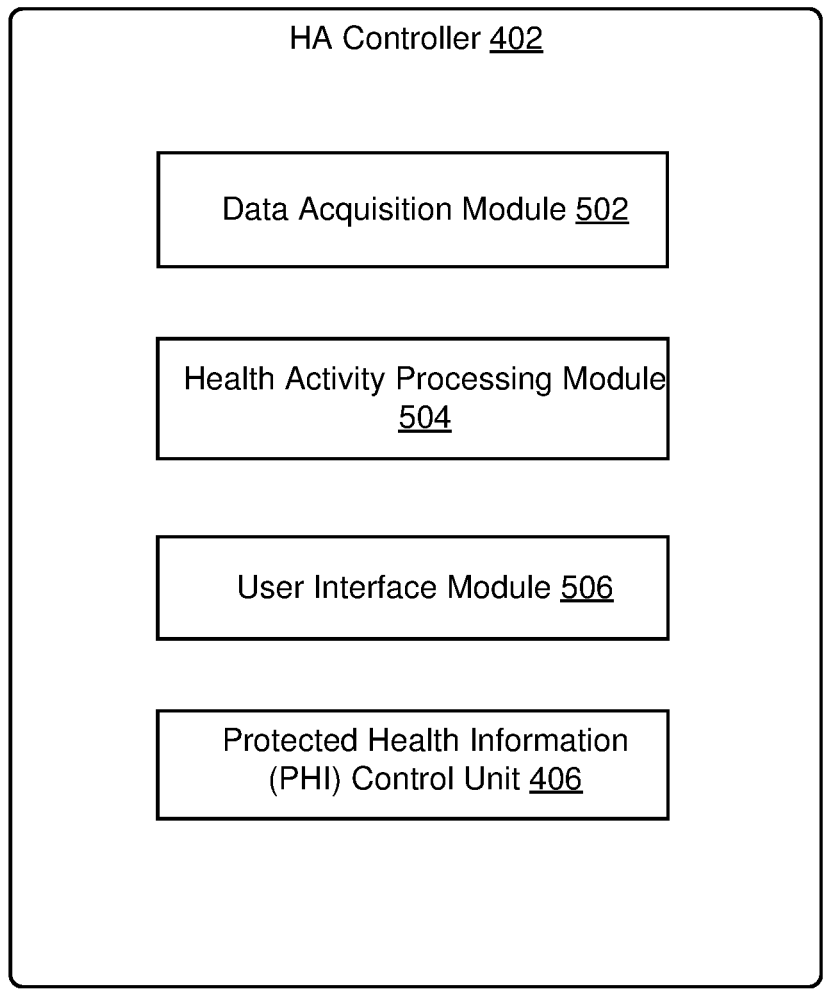
FIG. 5 is a block diagram illustrating an example health activity controller of FIG. 4 in accordance with the present disclosure.

FIG. 5 is a block diagram of an example health activity (HA) controller 402 as depicted in FIG. 4. In the illustrated implementation, the HA controller 402 includes a data acquisition module 502, a health activity processing module 504, a user interface module 506, and the PHI control unit 406.

The data acquisition module 502 is computer logic executable to receive and identify a health activity. For example, the data acquisition module 502 determines that a video received from a nurse is a baseline video of a patient walking into a clinic. In some implementations, the data acquisition module 502 may perform one or more algorithms to recognize at least one of text, image, video and audio data of the health activity. For example, the data acquisition module 502 applies a natural language processing approach to extract the text included in a health activity or performs a vision recognition algorithm to recognize a video of a certain patient. The data acquisition module 502 may also apply a machine learning method, an image processing method, etc., to identify the health activity. It should be understood that many other algorithms can be used to identify the data from the health activity.

The health activity processing module 504 is computer logic executable to analyze and process health activity data associated with the health activity. In some implementations, the health activity processing module 504 communicates with the data acquisition module 502 to identify the health activity data associated with the health activity. For example, responsive to the data acquisition module 502 determining that the health activity is a question about the bill of a patient's clinic visit, the health activity processing module 504 may determine information about a patient's previous visit and insurance information as associated health activity data. In other implementations, the health activity processing module 504 may receive health activity data included in a health activity. For example, the health activity processing module 504 receives a test result of a patient from a doctor's office.

In some implementations, the health activity processing module 504 cooperates with the blockchain health cloud 104 to determine whether the data can be recorded in a blockchain. For example, responsive to receiving a test result of a patient, the health activity processing module 504 combining with the blockchain health cloud 104 may add the test result to a blockchain such that one or more users can later access the data. In other implementations, the health activity processing module 504 may determine whether the data recorded in the blockchain can be viewed or accessed by a user. Responsive to a positive determination, the health activity processing module 504 may also retrieve the data for adding or accessing by a user. In some implementations, the health activity processing module 504 may use various technologies including the self-evolving blockchain contract code (as described below in FIG. 7) for acquiring and accessing control. The data acquire sequences and data accessing sequences will be described in detail with reference to FIGS. 9-13.

The health activity processing module 504 also processes the health data, which is described in detail below with reference to FIG. 9. The health activity processing module 504 may further track and monitor the health activities and associated data. For example, the health activity processing module 504 determines the resource of a health activity, e.g., a social media tool, and tracks the data from that resource. The health activity processing module 504 may also monitor the performance of a blockchain node or perform other analytics tasks based on the health data.

The user interface module 506 is computer logic executable to generate user interfaces to present a consistent and unified view for a user to input or view data. In some implementations, the user interface module 506 generates user interfaces to accept input regarding a health activity from the user. In other implementations, the user interface module 506 receives instructions from the health activity processing module 504, and sends graphical user interface data to the hardware device associated with the user causing the health data to be displayed on the hardware device. It is important to note that the user interface module 506 displays a consistent result regarding a health activity in a unified 2D or 3D view for a user no matter what hardware device is used by the user to handle the health activity. Example user interfaces are shown in FIGS. 15-19.

The PHI control unit 406 and its components will be described in detail below with reference to FIG. 7.

Figure 6:
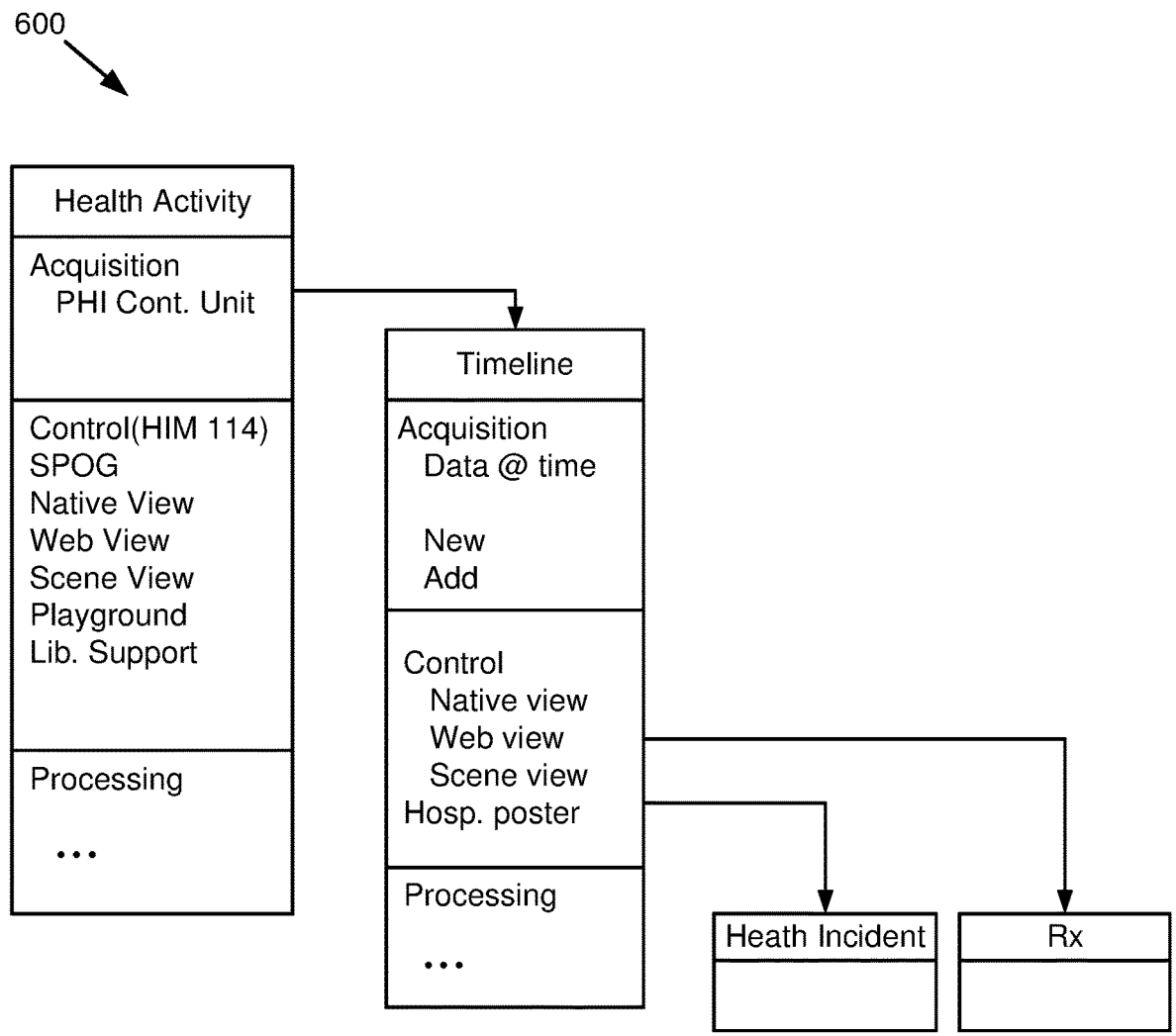
FIG. 6 is a graphic representation illustrating an example organization structure for object-oriented software to implement the functionality described in the present disclosure.

FIG. 6 is a graphic representation illustrating an example organization structure 600 for object oriented software to implement the functionality described in the present disclosure. The objects are organized in hierarchies to implement corresponding functions. In the example of FIG. 6, three hierarchies are shown. In the first hierarchy or level, a health activity object is created to implement the acquisition, control, and processing functions. For example, the health activity object may perform the control function by providing at least a native view, a web view, a scene view in user interfaces based on the support of SPOG, playground and library. The native view may be a view displayed through a user application. The web view may be a view displayed via a web browser. In some implementations, the web view includes a browser component created with a user's blockchain address and this address is used for access to the web view. The scene view may be a three-dimensional view displayed using augmented reality features or extended reality features.

An object includes one or more pointers to connect to one or more objects at the next level. As depicted in FIG. 6, the health activity object performs the acquisition function using a PHI control unit and connects to a timeline object using a pointer from the PHI control unit. The timeline object adds the new data based on timelines, provides support to different views including a hospital poster to a user, etc. The timeline object at the second level then uses a pointer to point to a health incident object and a prescription (Rx) object to implement the corresponding functions.

Figure 7:
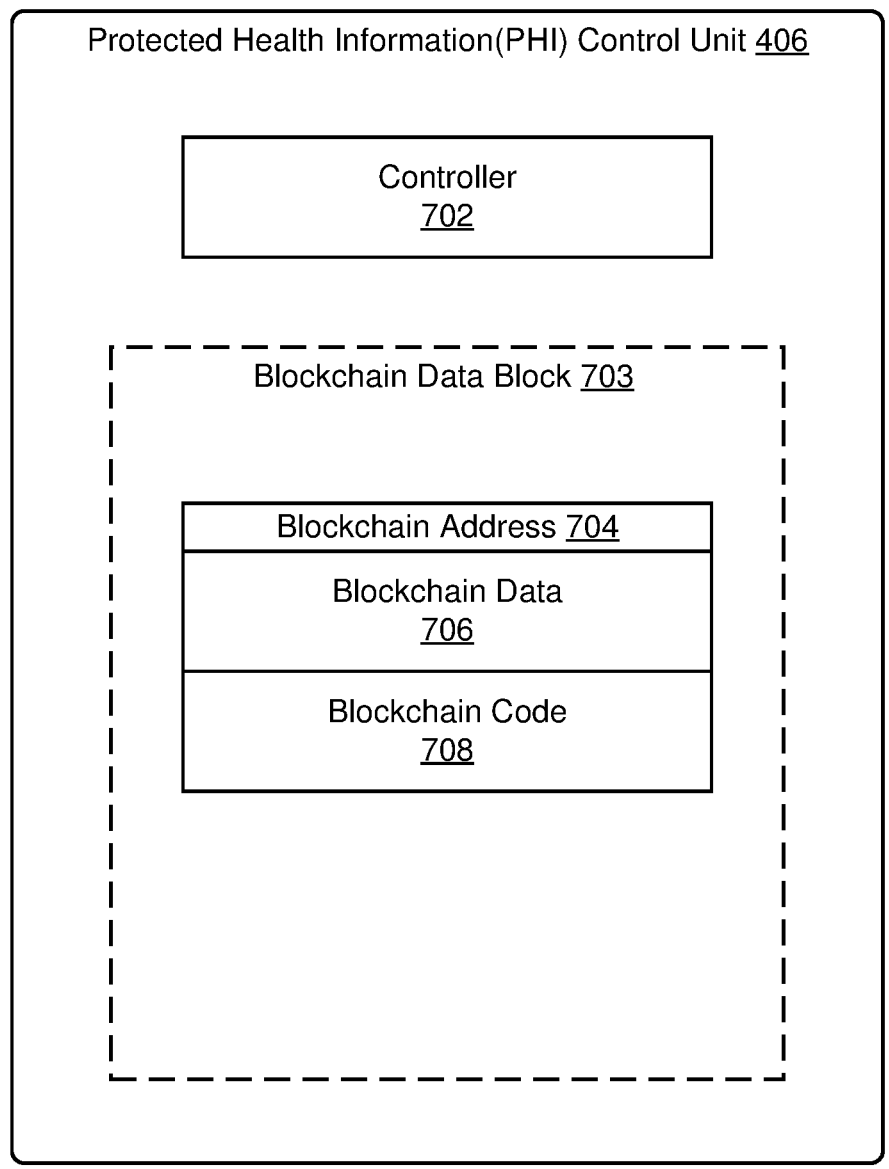
FIG. 7 is a block diagram of an example protected health information (PHI) control unit in accordance with the present disclosure.

FIG. 7 is a block diagram of an example protected health information (PHI) control unit 406. In the illustrated implementation, the PHI control unit 406 includes a controller 702 and a blockchain data block 703. The controller 702 is native to the HIM platform supported languages. The controller 702 controls the operation of the PHI control unit 406 to determine the access permission of users to specific health data by leveraging the access components such as blockchain health cloud 104 as described in FIG. 9-13. The blockchain health cloud 104 is advantageous since the blockchain nodes are connected to each other and form the infrastructure, and the blockchain nodes store, spread, and preserve the data to maintain the blockchain across all HIM devices needed to support the health activity.

In some implementations, a blockchain data block 703 includes a blockchain address 704, blockchain data 706, and a blockchain code 708.

The blockchain address 704 is a unique identifier of the corresponding blockchain data block. The use of the blockchain address will be described in the example data acquisition and access processes in FIGS. 10-13.

The blockchain data 706 represents the state of the blockchain data block at one instant in time. These data blocks are duplicated across all nodes 312/322 in the blockchain health cloud 104, where the data is stored at blockchain address 704 with its hash. A hash is a small-sized string computed using the raw data as input. The hash is modified when a transaction occurs, i.e., when the raw data or state is changed. The raw data is stored in a database or a file system in all nodes in blockchain health cloud 104. Therefore, using hashing utilizes the advantages of traditional storage mechanisms (e.g., querying database) while still getting the tamper-evidence of the blockchain. In addition, the small size of hashes reduces the transaction cost, e.g., lowering down network traffic and the use of other network and computer resources.

The blockchain code 708, in some implementations, is a smart contract. The smart contract is computer code or protocol deployed in a blockchain data block 703 that is then run in the nodes in 104 to manipulate its data or state. A state change or transaction specifies a function of the smart contract to be invoked. The contract starts working after a transaction addressed to it is submitted to the chain. Once a function is invoked and a smart contract is executed, i.e., a task is performed, the state or data is changed.

In some implementations, the blockchain data block 703 may be a data block storing the code at the blockchain address associated with a health activity, e.g., a user asking a question "when to refill medication X?" The blockchain data block 703 may also include code and data, where the code includes functions about how to interact with each customer technology (e.g., XR features used in interpreting a user's hand gestures), and functions about how to access a variety of resources. The blockchain data block may further be a data block associated with a health data user 106a . . . 106n. The blockchain data block includes a blockchain address for identifying a specific instance of a health activity unit 112. The blockchain address may be sent to a user via email, push notification, etc., and used by all users to interact with the blockchain. A user may use a smart device (e.g., a smartphone) and the blockchain address to exchange data in the blockchain health cloud 104. A user without a smart device (e.g., ambient users or users who interact through proxies), also referred to as a print user, may also process and share digital information within the blockchain health cloud 104 based on the blockchain address and voice/text input. The blockchain data block associated with a health data user may also include code that automates the communications with the user, even though traditional channels. Note that each blockchain data block, no matter it is a data block of a health activity, of a user, or of data, has a unique blockchain address used to identify the data block and interact with the data block.

Figure 8B:
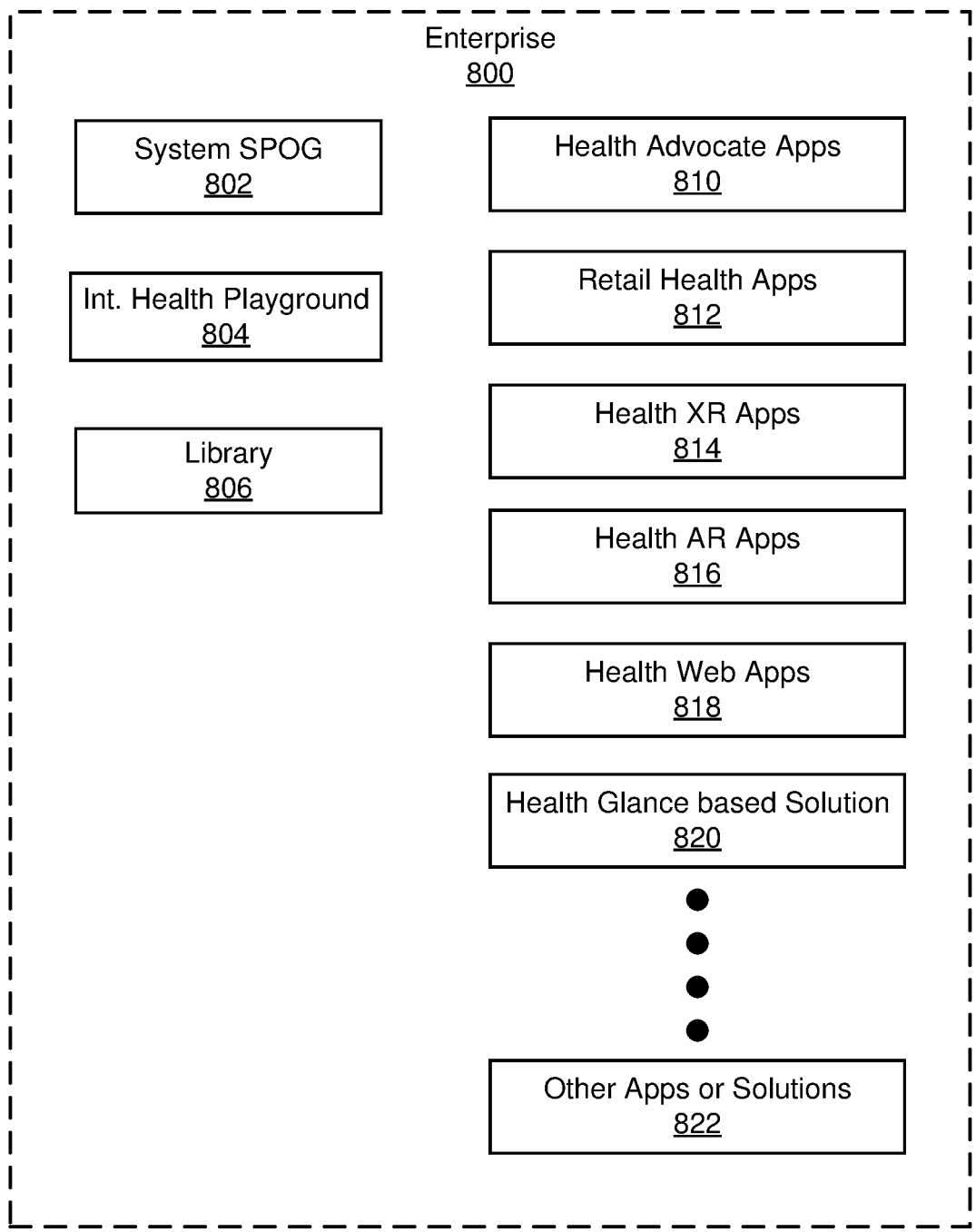
Figure 8C:
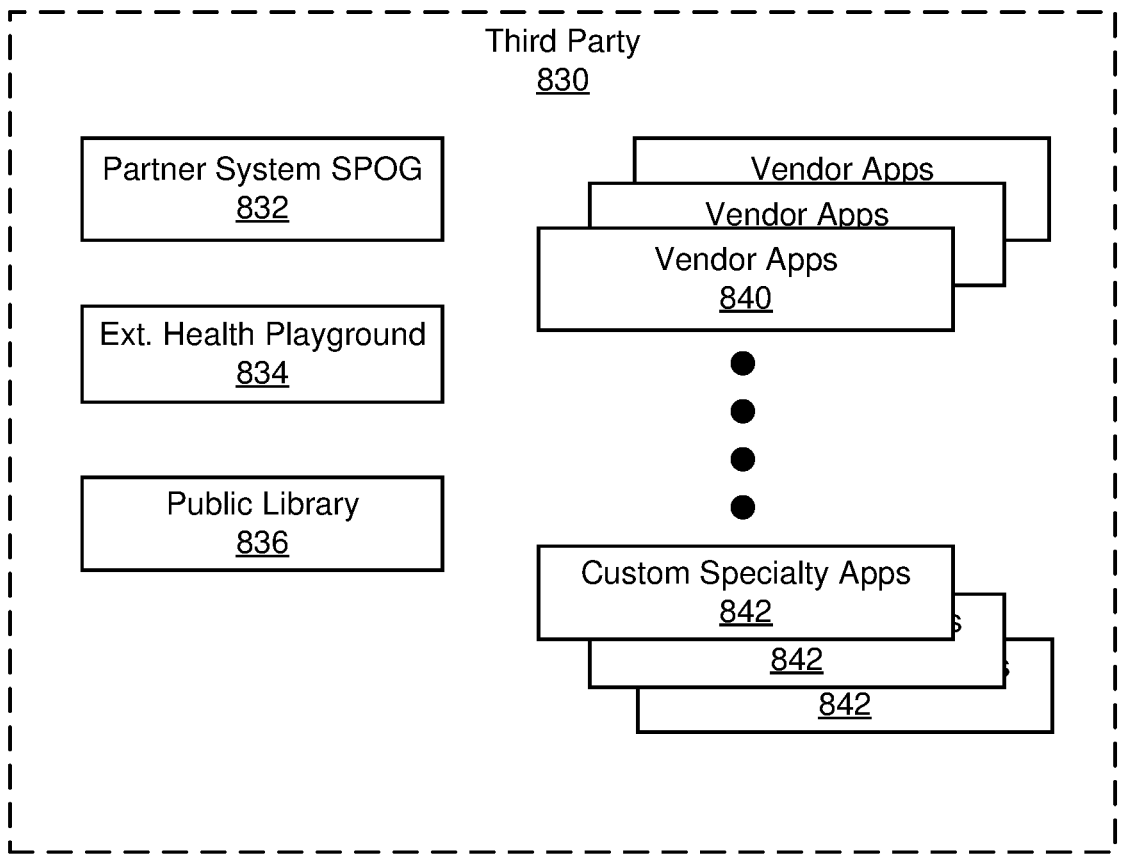

FIG. 8A-8C are block diagrams illustrating an example library & tools 116. The library & tools 116 include a collection of resources used by the health activity unit 112. As depicted in FIG. 8A and FIG. 1B described above, the library & tools 116 may be divided into two groups: enterprise 800 and third-party 830.

FIG. 8B illustrates example enterprise library & tools 800. As depicted, the enterprise library & tools 800 includes a system SPOG 802, an internal health playground 804, a library 806, health advocate applications 810, retail health applications 812, health XR applications 814, health AR applications 816, health web applications 818, health glance based solution 820, and other applications or solutions 822.

The system SPOG 802 includes software programs that assist in generating and providing a unified interface for displaying the health data within the internal domains of a healthcare entity. The internal health playground 804 includes resources used for producing and testing experiment code within the internal domains of the healthcare entity. The library 806 exposes the health activities features and tools added for the enterprise to leverage.

Figure 15:
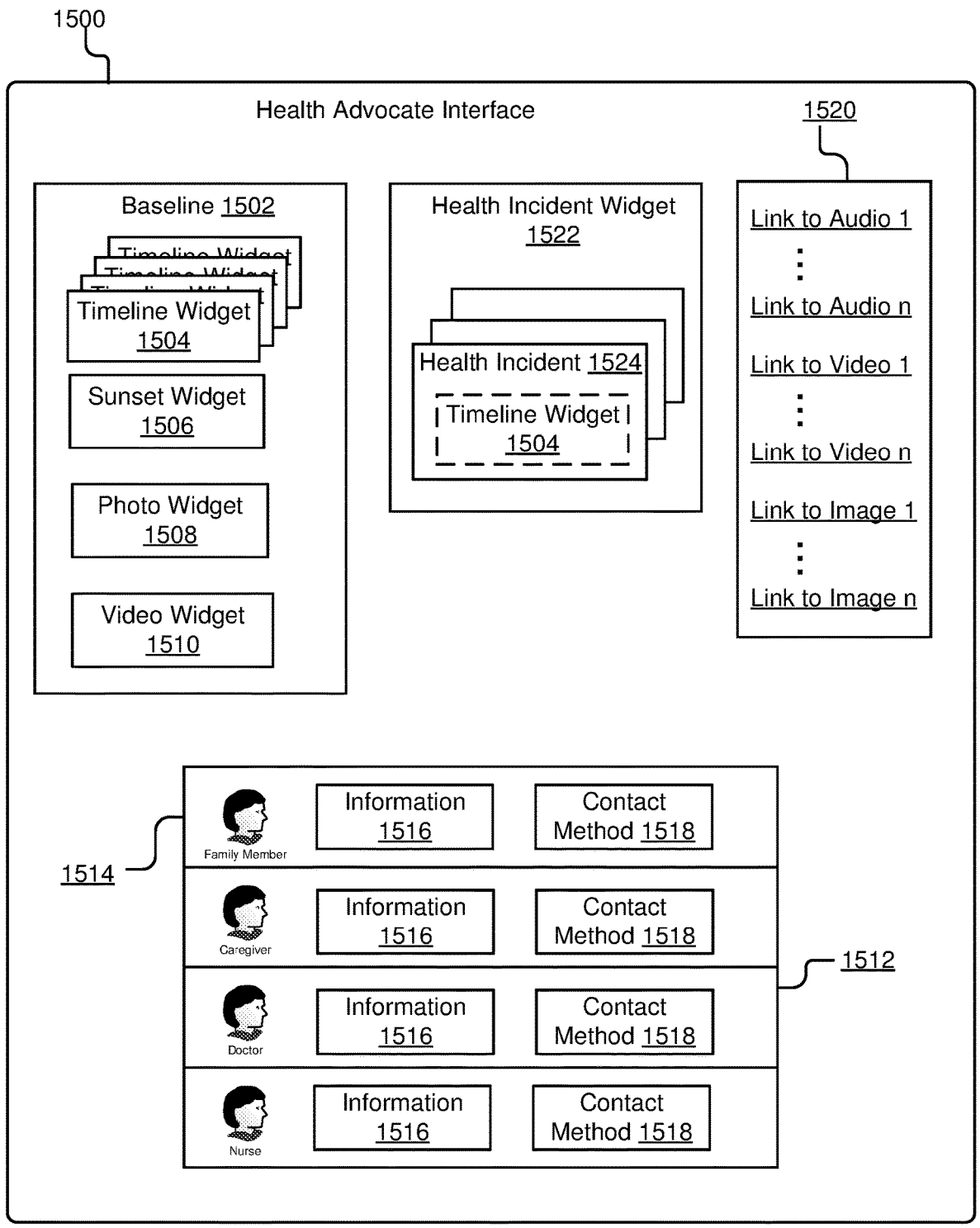
FIG. 15 is a graphic representation of an example health advocate interface in accordance with the present disclosure.

The health advocate applications 810 are software applications used by a caregiver or a guardian to communicate health activity data history associated with a patient to corresponding caretakers (e.g., the caretakers that pass by). The health activity data may be within the internal domains of the healthcare entity. For example, a nurse may upload healthy activity data of a patient through a health advocate application installed on her smartphone. A guardian may use the health advocate application to share the baseline information of a patient with the caregivers and to inform the caregivers about the share of information. In some implementations, the user interface module 506 in combination with the health advocate applications 810 and other components/resources may generate a health advocate interface as depicted in FIG. 15 to interact with health activity data.

One critical aspect of the health advocate applications 810 is that it is based on beginning interactions with ambient information channels to interact with the caretakers that pass by. For example, when an elderly patient goes to the hospital for a test, the health advocate applications 810 automatically capture the user health incidents and expose the incidents to the caretakers at a glance. Therefore, the health advocate applications 810 allow the entire 24-hour retesting of current health incidents (e.g., multiple duplicate CAT scans) and overnight hospital stay as well as corresponding expenses to be saved since the caretakers would have known that such conditions have already being treated.

The retail health applications 812 are software applications for retailers within the internal domains of the healthcare entity to exchange and process healthy activity data. For example, a retail health application 812 may allow a pharmacy to examine its inventory upon receiving medication refilling requests from users and to notify each user of the refilling status based on the inventory and the timeline of the requests being received.

The health XR applications 814 are software applications that utilize extended reality (XR) features to process and interact with healthy activity data. For example, for a user using a hardware device supporting the XR features, a health XR application installed on the device may communicate with the user interface module 506 to generate a user interface to take a user's body gesture, position, distance, etc., as input related to a health activity and output a 3D virtual scene for the user to access or view the health data associated with the health activity. The health XR applications 814 therefore allows modeling of the health activity data in real world objects (i.e., adding beads to a string for timeline events) by manipulation with hand gestures.

The health AR applications 816 are software applications that utilize augmented reality (AR) features to process healthy activity data. A health AR application 816 allows the patient to conduct different health activities in an augmented reality environment with a particular device, i.e., a smart glass. The health AR application 816 displays the health data in a 3D interface. This allows for the presentation of related Health information related to the patient in view.

The health web applications 818 are software applications that allow users to communicate health activities through a web-based interface, e.g., providing a web view via a web browser for display.

The health glance based solutions 820 are used to provide different views for health activity data. This can be used for timeline-based data representation. The health glance based solutions 820 may be displayed on various hardware platforms such as smart watches, televisions, color of home lights etc. In some implementations, these solutions are used along ambient communication channels.

There are also other applications or solutions 822 for processing and displaying the health activity data within specific domains of the healthcare entity.

Referring now to FIG. 8C, which illustrates example third-party library & tools 830. As depicted, the third-party library & tools 830 includes a partner system SPOG 832, an external health playground 834, a public library 836, vendor applications 840, and custom specialty applications 842.

The partner system SPOG 832 identifies the information that partners can publicly consume from the internal processing of health activities, i.e., the information allowed by enterprise for access, and provides the identified information to the partners. The external health playground 834 exposes the internal resources (e.g., experiment code) that is allowed for the partners to develop and produce, and test the experiment code in the outside domains of the healthcare entity. The public library 836 exposes the public health activities and the needed resources related to processing of the health activities in the outside domains of the healthcare entity. The vendor applications 840 are software applications used by vendors to communicate health activity data. The custom specialty applications 842 are software applications that the vendors create and support for handling health data related to customer specialties. The vendor applications 840 and the custom specialty applications 842 process the health data from third-party domains.

Figure 9:
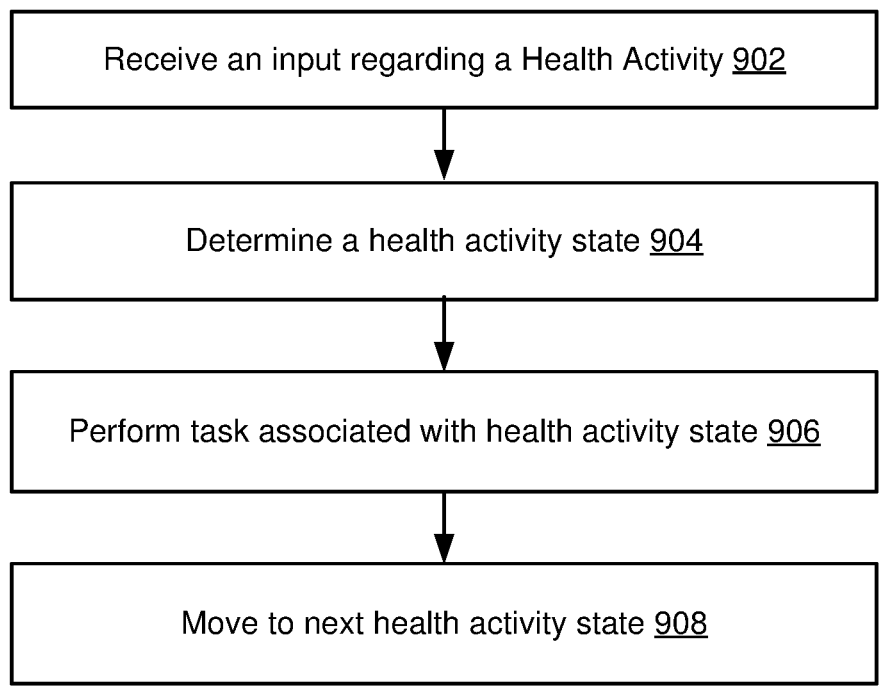
FIG. 9 is a flow diagram illustrating a general method for processing a health activity in accordance with the present disclosure.

FIG. 9 is a flow diagram of a general method for processing a health activity. At step 902, the PHIVC system 110 including the health activity processing module 504 receives input regarding a health activity. For example, after a patient visited a doctor, the doctor added a prescription of a new medication and wanted to enter the prescription into his medical records system for the patient. The input regarding a health activity is the new prescription related to the patient's visit.

At step 904, the PHIVC system 110 determines a health activity state. In some implementations, the health activity state is the state of a blockchain data block associated with the health activity. The state is changed when a transaction occurs or a task is performed.

At step 906, the PHIVC system 110 performs a task associated with the health activity state. Continuing with the above example, the task associated with the health activity state is to enter the new prescription, i.e., to write data of the new prescription to the blockchain. To perform the task, the blockchain code included in the blockchain node, for example, a smart contract, is executed.

At step 908, the PHIVC system 110 moves to a next health activity state. Once the smart contract is executed, the task of recording the new prescription is performed. As a result of the task being performed, the state of the blockchain data block is changed, i.e., moved to a next health activity state.

Figure 10:
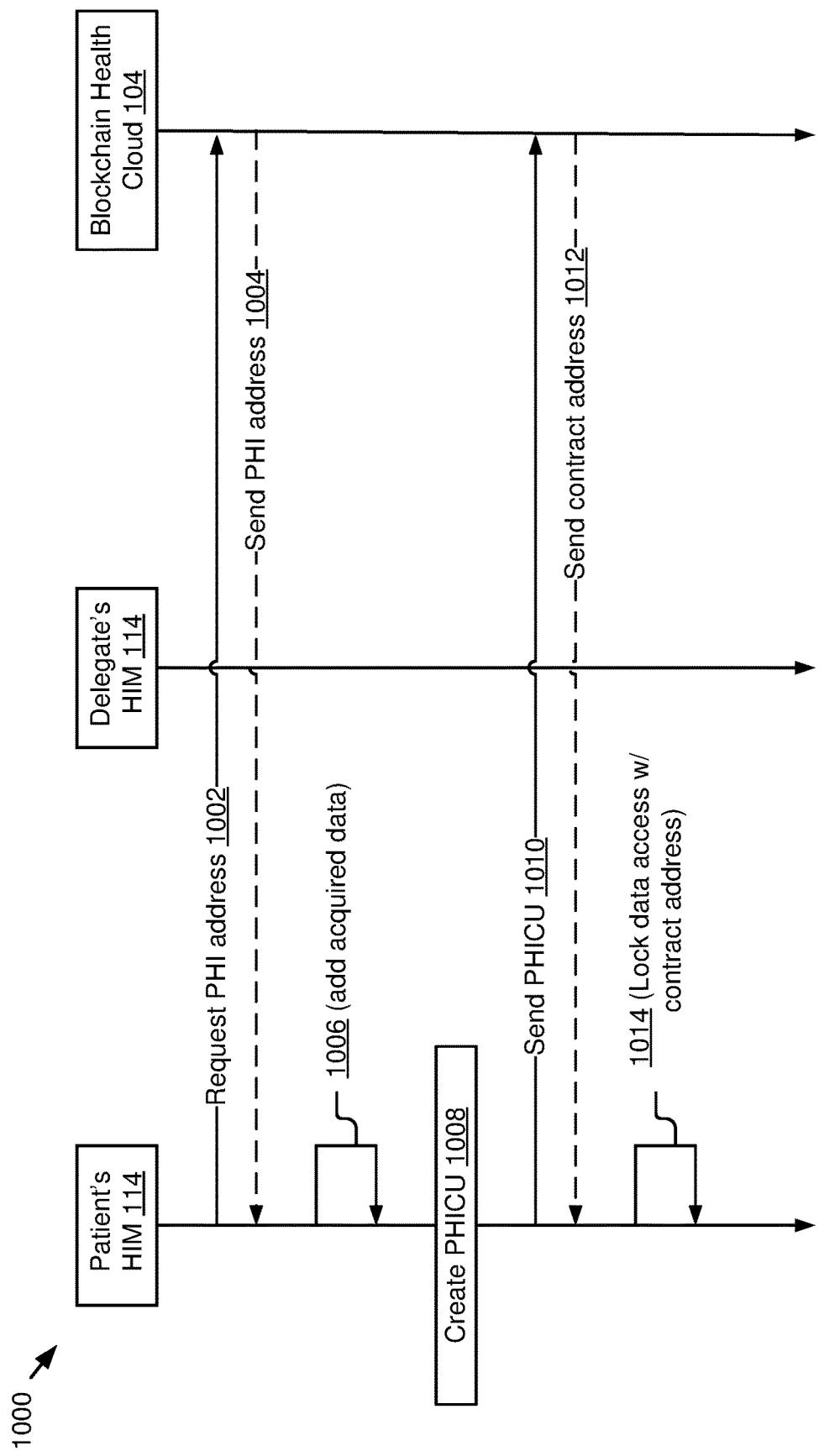
FIG. 10 is a flow diagram of a method for creating a PHI control unit (PHICU) for a patient and acquiring data from the patient in accordance with the present disclosure.

FIG. 10 is a flow diagram of a method 1000 for creating a PHI control unit (PHICU) for a patient and acquiring data from the patient. The PHICU is associated with a particular health activity from the patient and is used to control user access to the health data of the health activity. This figure shows how to acquire health activity data of a patient from the patient himself/herself, where no third party or delegate is involved and therefore no right is granted to a delegate.

At step 1002, a patient's human activity module (HIM) 114 sends a request for a PHI address to the blockchain health cloud 104. In some implementations, the patient's HIM 114 requests the PHI address responsive to receiving a health activity from the patient, for example, changing his pharmacy to a different location. Once the blockchain health cloud 104 receives the request, at step 1004, it sends the requested PHI address back to the patient's HIM 114. In some implementations, the PHI address is a wallet address. The wallet address may be a string of random letters and numbers (e.g., a public key) that acts as a username to identify the patient.

At step 1006, the patient's HIM 114 adds the acquired data to the chain. In some implementations, the patient's HIM 114 communicates with the HA controller 402 to acquire the health data from the health activity of the patient. At step 1008, the patient's HIM 114 creates a PHICU. At step 1010, the patient's HIM 114 sends the PHICU to the blockchain health cloud 104. As a response, at step 1012, the blockchain health cloud 104 sends back a contract address associated with the PHICU to the patient's HIM 114. As illustrated in FIG. 7, the PHICU includes a blockchain address, a blockchain data, and a blockchain code. The blockchain code may be a smart contract. When the contract is deployed, it is allocated at a unique address, i.e., a contract address. At step 1014, the patient's HIM 114 locks the data access with the contract address. The contract allocated at the contract address is configured to be executed when a condition is invoked. A set of conditions may include access restrictions.

Figure 11:
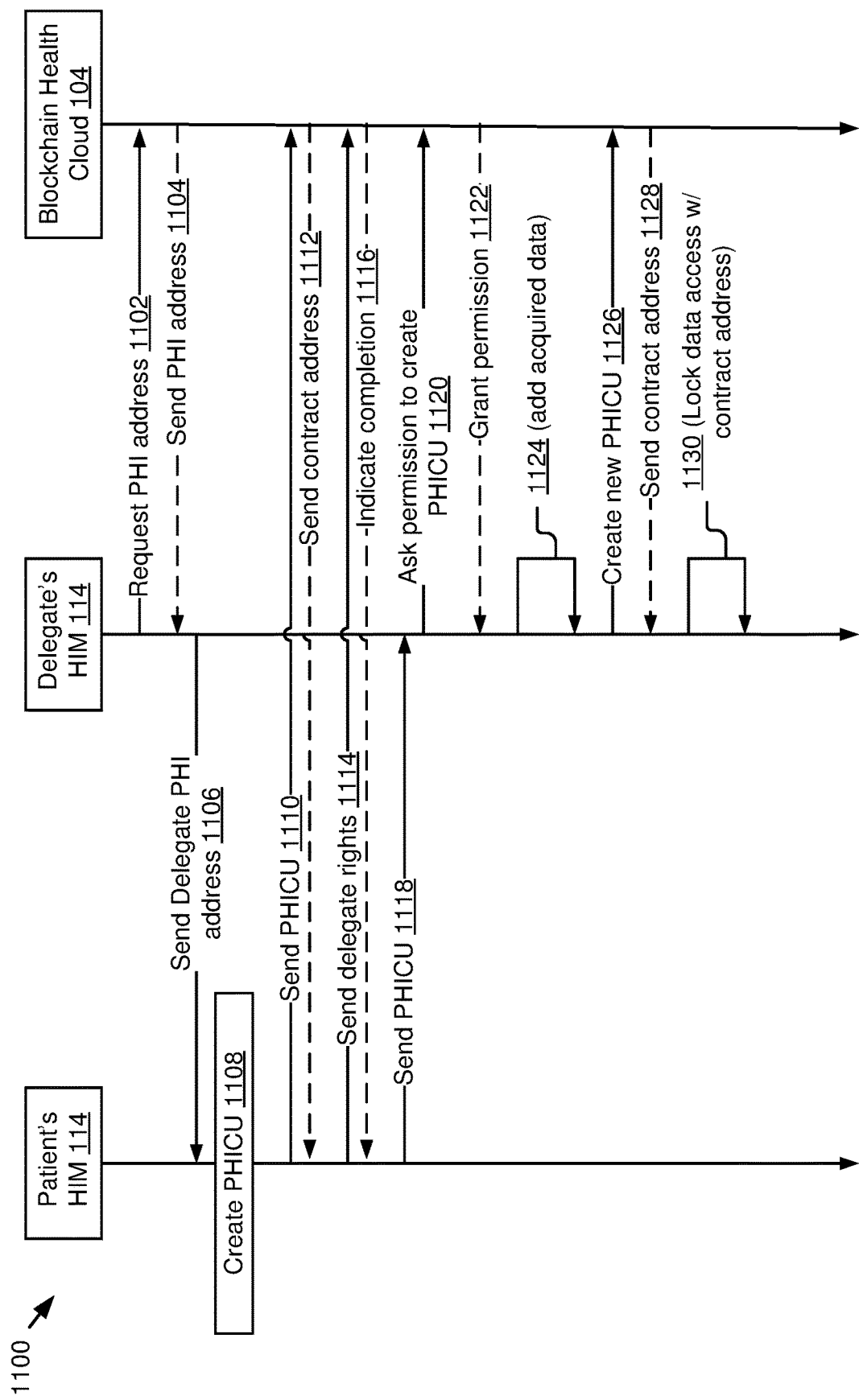
FIG. 11 is a flow diagram of a method for creating a PHICU for a delegate on behalf of a patient and acquiring data from the delegate in accordance with the present disclosure.

FIG. 11 is a flow diagram of a method 1100 for creating a PHI control unit (PHICU) for a delegate on behalf of a patient and acquiring data from the delegate. As shown in this figure, a patient grants rights to a delegate based on authorizing the PHICU so that the delegate can acquire health activity data of the patient on behalf of the patient. For example, a patient may grant permission to a nurse to add a baseline video of the patient walking into the clinic to the blockchain. In some implementations, the delegate may be an individual such as a nurse, a doctor, etc. In other implementations, the delegate may include a domain such as a RX pharmacy benefit management (PBM) system.

In order to add the patient's health activity data to the chain, at step 1102, a delegate, e.g., the nurse, sends a request for a PHI address (e.g., a wallet address) to the blockchain health cloud 104 via the delegate's HIM 114. At step 1104, the blockchain health cloud 104 sends the requested PHI address back to the delegate's HIM. Once receiving the PHI address, at step 1106, the delegate's HIM sends this delegate PHI address to the patient's HIM for authenticating. By doing this, the delegate notifies the patient to start an authorization process on the chain to allow the delegate to act on behalf of the patient.

At step 1108, the patient's HIM creates a PHICU based on the delegate PHI address. The PHICU is empty because the patient would not add any blockchain data. At step 1110, the patient sends the PHICU to the blockchain health cloud 104. As a response, at step 1112, the blockchain health cloud 104 sends back the contract address of the PHICU to the patient's HIM. No contract on the chain other than the contract of the PHICU can be allocated to this address. The patient's HIM may configure the contract to set up the access restrictions including delegate rights for the delegate. For example, the patient's HIM may tell the contract allocated at the contract address that the PHI address is allowed to acquire the health data of the patient. At step 1114, the patient's HIM sends the delegate rights to the blockchain health cloud 104. At step 1116, the blockchain health cloud 104 sends back a completion indication to the patient's HIM, which indicates that the patient has completed passing access control or granting rights to other levels (e.g., the delegate) and the communication between the patient's HIM and the blockchain health cloud 104 ends.

At step 1118, the patient's HIM sends the PHICU to the delegate's HIM. Responsive to receiving the PHICU, at step 1120, the delegate's HIM asks the permission to create a new PHICU for the patient from the blockchain health cloud 104. At step 1122, the blockchain health cloud 104 grants permission to the delegate's HIM based on the delegate rights granted by the patient. At step 1124, the delegate's HIM adds the acquired data to the blockchain. The acquired data is associated with the health activity of the patient and is added by the delegate on behalf of the patient based on the delegate rights authorized by the patient. At step 1126, the delegate's HIM creates the new PHICU 1126. This new PHICU is associated with the health activity. At step 1128, the blockchain health cloud 104 sends the contract address to the delegate's HIM. At step 1130, the delegate' HIM locks the data access with the contract address. Note that the delegate's HIM can continue to add data to the PHICU it created.

FIGS. 10 and 11 explore and describe two scenarios for the acquisition of data. In FIG. 10, when the health data is added to the blockchain by the patient, the data is stored in a database residing in the patient's domain. In FIG. 11, when the health data is added to the blockchain by the delegate, the data is stored in a database residing in the delegate's domain. Depending on different delegates, the delegate's domains are different. For example, if the delegate is a doctor, the delegate's domain is a hospital domain. Generally, in a blockchain ecosystem, the stored data is retrieved or captured on the domain it was added to and the PHI level of access is kept in a PHICU contract. This allows the blockchain to leverage all domains that are used in the healthcare world.

Figure 12:
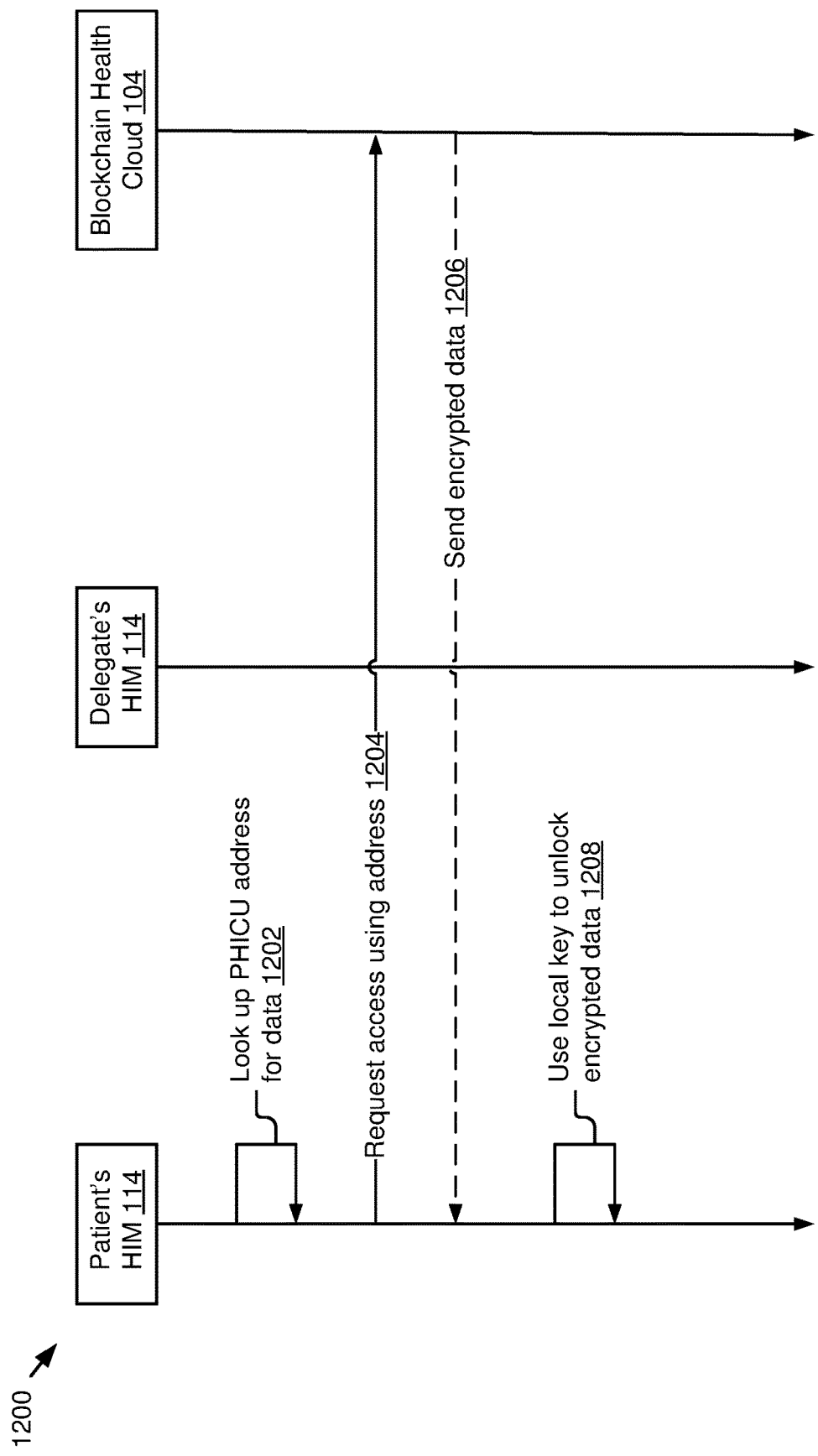
FIG. 12 is a flow diagram of a method for a patient accessing or viewing health activity data in accordance with the present disclosure.
Figure 13:
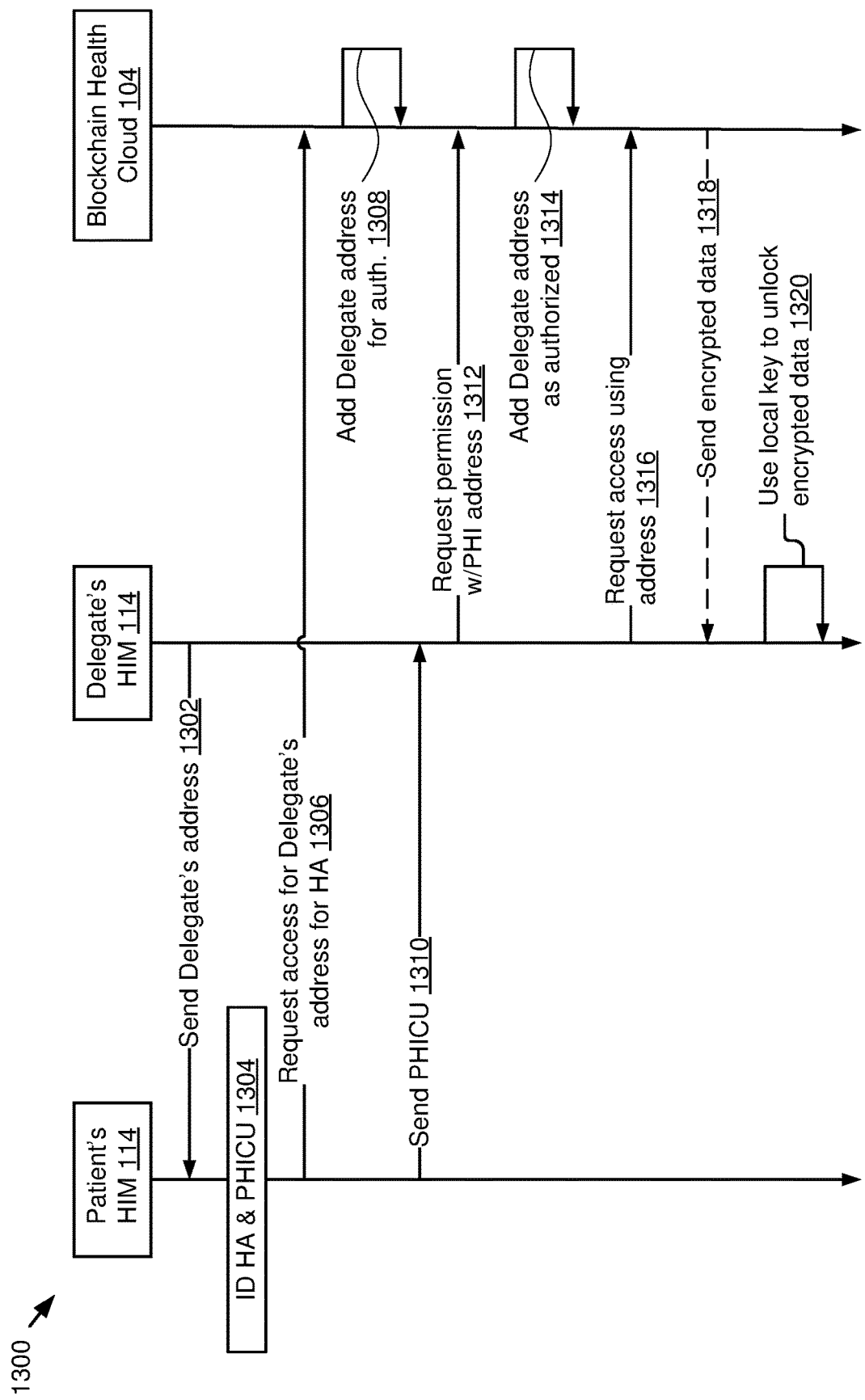
FIG. 13 is a flow diagram of a method for a delegate accessing or viewing health activity data in accordance with the present disclosure.

FIGS. 12 and 13 depict the sequences for users to view or pass on rights to view health activity data. Referring to FIG. 12, which is a flow diagram of a method 1200 for a patient accessing or viewing health activity data. Using this method, a user can control his/her own health activity data in the blockchain system. At step 1202, the patient's HIM looks up the PHICU address for data. At step 1204, the patient's HIM sends a request for accessing the data using the PHICU address. At step 1206, the blockchain health cloud 104 sends the encrypted data back to the patient's HIM. For example, the blockchain uses a cryptographic hash to encrypt data to protect the data from being tampered. At step 1208, the patient's HIM uses the local key to unlock the encrypted data. The local key is used in a local domain, i.e., the domain to which the patient has physical access via a hardware device, to access the data stored in the local domain.

FIG. 13 is a flow diagram of a method 1300 for a delegate accessing or viewing health activity data. In this figure, a patient gives rights to the delegate to view or access the data. At step 1302, a delegate's HIM sends a delegate's address to the patient's HIM. In some implementations, the delegate's address is a wallet address that identifies the delegate. The address may be physically sent to the patient, for example, by email or push notification displayed on a hardware device associated with the patient. Because patients physically hold their addresses or keys to the root of their health data, data security is improved.

At step 1304, the patient's HIM identifies the health activity and PHICU associated with the health activity. In some implementations, the patient's HIM 114 communicates with the HA controller 402 to recognize health activity data, for example, using a voice recognition approach to identify the activity being a question about whether a patient is allergic to certain medication and determining that at least the patient's medical record is associated with this health activity.

At step 1306, the patient's HIM requests access for the delegate's address for the health activity from the blockchain health cloud 104. At step 1308, the blockchain health cloud 104 adds the delegate's address for authorization. At step 1310, the patient's HIM sends the PHICU to the delegate's HIM. In some implementations, the patient's HIM may physically send the PHICU, for example, by email or by service call. The patient's HIM only sends the PHICU to a delegate that the patient wants to give access to. Therefore, by sending the PHICU to the delegate's HIM, the patient's HIM has agreed to assign rights to the delegate for accessing the data. The rest of the process is for informing the blockchain health cloud that the delegate is authorized to access data and actually retrieving the data from the blockchain health cloud for the delegate to view.

At step 1312, the delegate's HIM requests the permission with the PHI address from the blockchain health cloud 104. At step 1314, the blockchain health cloud 104 adds the delegate address as an authorized address. At step 1316, the delegate's HIM sends a request for accessing the data using the delegate address. Once receiving the request for data access using the delegate address and determining that this address has been authorized, at step 1318, the blockchain health cloud 104 sends the encrypted data back to the delegate's HIM. At step 1320, the delegate's HIM uses the local key to unlock the encrypted data for the delegate to view.

Figure 14:
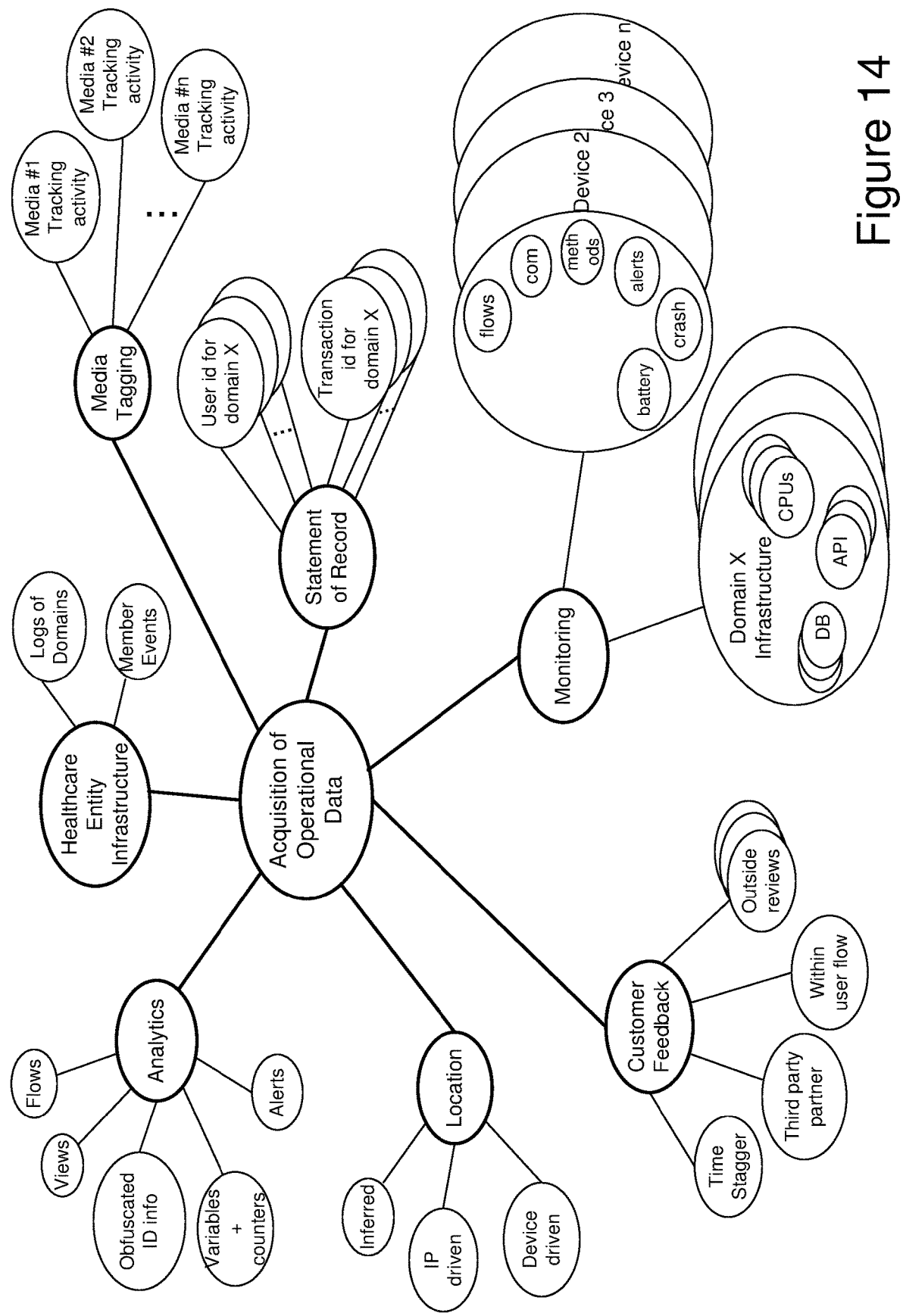
FIG. 14 is a graphic representation of an example views of a single pane of glass (SPOG) for viewing health data in accordance with the present disclosure.

FIG. 14 is a graphic representation of an example of acquiring health data for generating views of a single pane of glass (SPOG). As illustrated in FIG. 14, the operational data or the health data is identified to be associated with health activit(ies) and displayed through SPOG on different types of devices (including devices supporting 3D display using XR or AR features) in a consistent and unified view. For example, the operational data may include location data. The location data may be inferred data, IP-driven data, and device-driven data. The inferred data may imply a user's location, for example, the user must be in office because it is 10 am on Thursday. The IP-driven data may indicate a user's location because an IP address of a user device associated with the user places the user in a specific location. The device-driven data may tell a user's location through device information, for example, a global positioning system (GPS) signal of the user's cellphone.

The operational data also includes data from analytics, customer feedback, monitoring, media tagging, statement of record, and healthcare entity infrastructure. For example, the data from healthcare entity infrastructure may include data from CVS® Pharmacies, specifically, data retrieved from logs of domains and data describing member events. The monitoring data may include data from tracking and monitoring different types of hardware devices accessed by users. The hardware devices may include smart glasses, smart phones, tablets, automobile computers, etc. As depicted in FIG. 14, the monitoring data may include data about a health activity such as battery or crash received from the monitoring of user devices. The monitoring data may also include data from monitoring domain infrastructure, for example, activities and performance of hardware devices, software applications, databases, etc., in a domain. A wide range of operational data or health data supports accurate analysis and rich content for views of the SPOG, and therefore increases efficiency and improves performance.

FIG. 15 is a graphic representation of an example health advocate interface 1500. The health advocate interface 1500 is intended to ambiently start all interactions of the patient-related health activities with the people who pass by the patient. The health advocate interface 1500 allows users (e.g., caregivers, health providers, guardians, family/friends) to interactively communicate various health activity data associated with the patient. These activity and relationships to user addresses are grouped into and not limited to a suite of tools for baseline, health incidents, entertainment and communications. In some implementations, the user interface module 506 cooperating with the health advocate applications 810 and other components of the system 100 generates the health advocate interface 1500. The health activity data used for generating the health advocate interface 1500 may be retrieved based on various PHICU access control for all the related health activities within the blockchain health cloud 104 and collected from different healthcare-related resources (e.g., a hospital database) and healthcare-unrelated resources (e.g., social media).

In some implementations, the health advocate interface 1500 operates in two modes: a view mode and a control mode. In the view mode, the health advocate interface 1500 allows users to view the data in different views. In the control mode, the health advocate interface 1500 allows users to take actions, for example, adding a photo to a photo cloud, sending an email to notify a user about a patient's most recent health activity, or invoking a user interface to take a next step action, etc. In some implementations, the health advocate interface 1500 includes clickable button(s) (not shown) in different widgets for the users to select for triggering execution of specific actions.

The health advocate interface 1500 includes a baseline 1502. The baseline 1502 includes the view widgets of the related baseline health activities that record patients' health activity data and provide visible measures of patients' conditions for browse and view by the users. The baseline 1502 may serve as a reference point and crucial basis for performance analysis and other complex analytics tasks. In some implementations, the baseline 1502 takes the health activity data as input and updates different views to provide the most recent information to users. As depicted in FIG. 15, the baseline 1502 includes one or more timeline widgets 1504, a sunset widget 1506, a photo widget 1508, and a video widget 1510.

A timeline widget 1504 is a tool that models health activity data over time. Multiple timeline widgets 1504 perform timeline control over health activity data of the patient across one or more timelines. The basis of timelines is that the timeline widget 1504 can add them together to create sets that users can interact with. A timeline may be based on hours, days, weeks, months, or years.

The timeline widget 1504 may create a single timeline to record a health activity's pattern of data for the patient over time. For example, a timeline may show the patient's sleep habits, i.e., when they go to sleep and when they wake, which is similar to data taken from a breath treatment of continuous positive airway pressure (CPAP). The timeline widget 1504 may also combine separate timelines for each type of health activity for the patient over time. For example, the timeline widget 1504 supports the interaction with a set of medication timelines that shows at what time a patient took what medication, and generates a combined timeline made up of the individual health incident timelines for each activity the medication addresses to show at what time they occurred for that health incident. The medication timeline may be based on hours such as showing that the patient took medication X at 8:10 am. The health incident timeline may be based on days such as showing that the patient broke her leg on one day and the other days the user goes to rehab as these are all related to this health incident.

In addition to the applications of the advocate interface, these timeline widget(s) 1504 may also integrate the health activity data associated with multiple patients to create one or more timelines. For example, the timeline widget(s) 1504 generates a medication timeline to show that patient A took medication X, then patient B took medication X, then patient C took medication Y, and so forth. Or the timeline widget(s) 1504 may generate a first medication timeline for medication X to show at what time different patients took medication X and generate a second medication timeline for medication Y to show at what time different patients took medication Y. It should be understood that other types of timelines, e.g., timelines for activities of users other than patients, are possible.

The timeline control is data-driven. The timeline widget 1504 updates the timeline when new data is received over time for that incident, for example, inserting the rehabilitation treatments into the broken leg incident where the health data is newly received to a time point of an existing timeline or adding the incident to extend the timeline to a new time point. The timeline widget 1504 also communicates with other components of the system 100 to generate user interfaces to show the timelines in different views. The timeline widget 1504 may also control how a user views (e.g., pinches, zooms) a timeline, selects a timeline or its element, etc., in different views. The different views of timelines will be described below with reference to FIGS. 18A-18C and 19A-19B.

In addition to the timeline widget 1504, the baseline 1502 also includes widgets 1506-1510. The sunset widget 1506 will be described below in FIG. 16. The photo widget 158 retrieves photos from different resources and presents the photos to users in different views. The photo widget 158 also allows the user to add photo(s) to a photo cloud. Similarly, the video widget 160 displays videos in different views and provides interface(s) for a user to add video(s) to a video cloud. The user interfaces that display the photos/videos in various views are described below with reference to FIGS. 17A-17C.

As depicted in FIG. 15, the health advocate interface 1500 also includes one or more health incident widgets 1522, which manages multiple health incidents 1524 for the patient. The health advocate interface 1500 shows the patient health history from a health incident perspective (e.g., broken leg, auto accident, walking Pneumonia). In some implementations, the health incident widget 1522 may communicate with the health activity processing module 504 and/or other components of the system 100 to identify and analyze the data associated with a health incident/activity from the received data, and to control user interactions with the identified data. Since health incidents are extensions of timelines as shown in FIG. 6, in some instance the health incident widget 1522 may also leverage a timeline widget 1504 (as depicted in FIG. 15) to control how a user views (e.g., slides or pinches) a health incident on a timeline, selects the health incident on the timeline, or performs other operations on the health incident.

The health advocate interface 1500 also provides links to audio, video or images 1520 for users' knowledge or for entertainment. This knowledge can be used as immediate links to interact with and show to other users or passers by. For example, after a patient was notified of a specific disease related to the patient through the communication widget 1512, he may want to know more about this disease through the links 1520. Or a mother merely wants to make sure, while her child is in the hospital, that the caretakers have immediate access to the entertainment that the child enjoys through the actions 1520, i.e., opening the entertainment when the links are selected. In some implementations, the video, audio, images are from different resources, e.g., a database in a third-party domain, a website, or Internet.

The health advocate interface 1500 uses the communication widget 1512 to communicate with users and caretakers passing by about a patient's condition determined based on the health activity data of the patient. In the illustrated implementation, the communication widget 1512 includes a list 1514, information 1516, and contact methods 1518.

The list 1514 includes the identifiers of users that need to know certain conditions of the patient. The users may be a family member, a caregiver, a doctor, a nurse, etc. The communication widget 1512 automatically sends the information 1516 to the users responsive to receiving a user interaction, receiving a health accident, determining a patient condition, etc. The communication widget 1512 may provide different information 1516 to different users based on the context (e.g., a type of user interaction) and identities of users. For example, responsive to receiving a blood test result of a patient, the communication widget 1512 sends a notification to the patient's guardian as information 1516. But no message is sent to the primary care provider (PCP) of the patient since nothing in the result needs to bring the PCP's attention. The communication widget 1512 may include a full list 1514 of users to be contacted and leave the information 1516 associated with one user in the list (e.g., the above PCP) blank when there is no information delivered to the one user. Or the communication widget 1512 may generate a list 1514 of recipients of information and display each specific information 1516 to a corresponding recipient on the list 1514. For example, one view of the logic to decide if a user shows on the list 1514 is merging the users related to the active health incidents for the patient with any users that have open communications. This makes what is displayed on 1514 responsive to receiving a health activity state changes, such as when a health activity sends an email to the PCP, sends a push notification to a doctor's smart watch and smart phone, and sends another push notification to a nurse's smart phone the communication widget 1512 is automatically updated.

A contact method 1518 defines how a user wants to be contacted. The communication widget 1512 may determine the contact method 1518 based on a user's preference, the user's habits, a hardware device associated with the user, regulations or rules (e.g., made by a healthcare organization), etc. The communication widget 1512 may retrieve data about the user's preference or habits or associated hardware device from the a blockchain data block associated with the user using the PHICU from the blockchain. For example when a the patient or a caretaker passing by wants to communicate with a user in the list 1514, the contact control checks with the user's PHICU and opens the appropriate controls for communication.

In addition to sending the information 1516 to individual users using the preferred contact methods 1518, the communication widget 1512 may also reflect messages delivered in a custom system according to a specific rule. For example, an active health incident contains the rule that changes in the baseline information of the patient will be sent to relevant caregivers/guardians and a hospital poster when the patient is sent to an emergency room with an ambulance. Therefore, the communication widget 1512 may similarly reflect the baseline information that was sent to a family member and a caregiver and was also emailed to the PCP. The information display on printed media optimizes the information transmission as every user that needs to be contacted will receive the information electronically or by paper.

In some implementations, the communication widget 1512 may communicate with a user in real time upon receiving a user interaction. In other implementations, the communication widget 1512 may work with the timeline widget 1504 to contact a user in a time staggered way. For example, caregiver A added a video of a patient's activities to baseline data of the patient. After a first time interval, the communication widget 1512 may push a notification to caregiver A to take a new video of the patient. Or caregiver B conducted a medical evaluation of the patient. After a second time interval, the communication widget 1512 may email caregiver B to reevaluate the patient.

Figure 16:
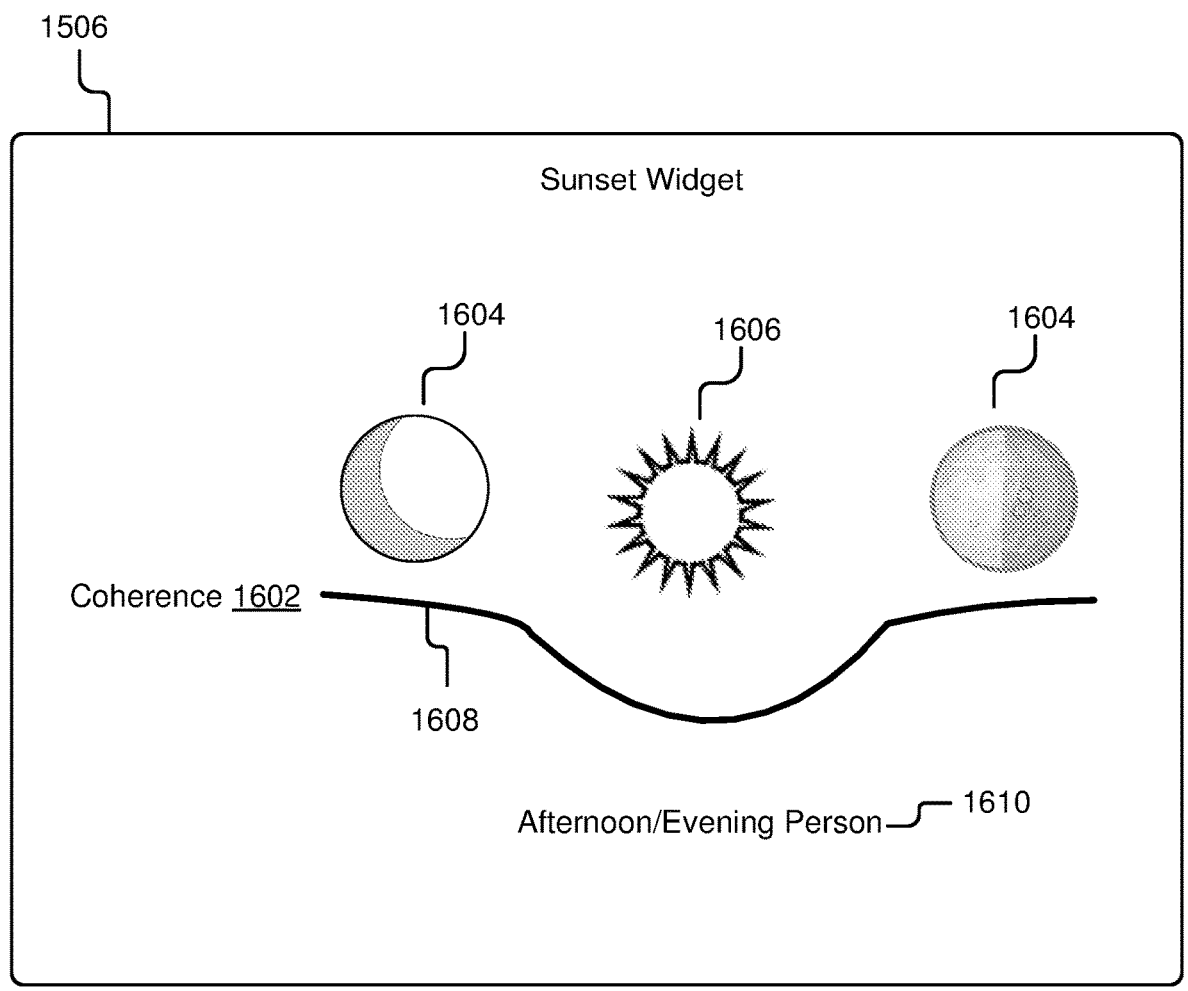
FIG. 16 is a graphic representation of an example sunset widget in accordance with the present disclosure.

FIG. 16 is a graphic representation of an example sunset widget 1506 included in the health advocate interface of FIG. 15. The sunset widget 1506 may use a patient's baseline information about sleeping, talking, walking, and other conditions as coherence factors to determine a coherence level 1602 of user activities/conditions at a time of the day. As the coherence curve 1608 explains, this patient is more active in the night 1604 than during the day 1606. Therefore, the sunset widget 1506 determines that this patient is an afternoon/evening person 1610. In some implementations, the sunset widget 1506 may also communicate with the baseline 1502 to adjust the timeline and associated baseline information, for example, by adding or removing time intervals of the timeline. The sunset widget 1506 may then use the adjusted information to refine the coherence level.

Whether a patient is an afternoon/evening person or a morning person is useful to determine what time is a good time to interact with the patient. Note this is a LIFE SAVING INTERACTION. For example, a correct time to interact with a patient may significantly affect the treatment of the patient. For an afternoon patient in the hospital, a doctor may conclude that she needs to be sent to palliative care based in their short morning shift interaction. However, after seeing the patient in the afternoon, the doctor may think that the patient will recover and send the patient to rehabilitation treatment. This example highlights doctor interactions that were postponed from a bad time to a good time, and since the prognosis was rehabilitation, this is also considered as a LIFE Saved.

Figure 17A:
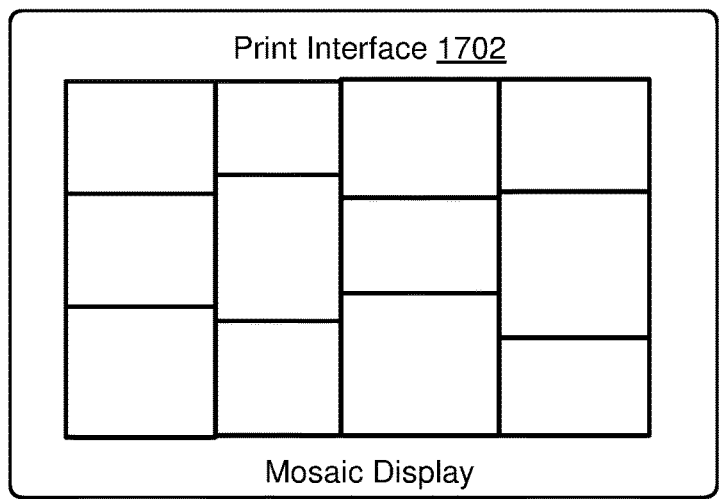
FIGS. 17A-17C are graphic representations of example interfaces for displaying photos/videos in accordance with the present disclosure.
Figure 17B:
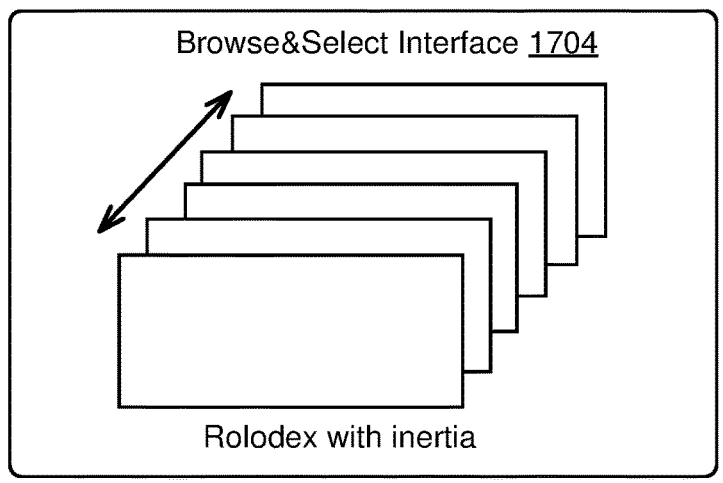
Figure 17C:
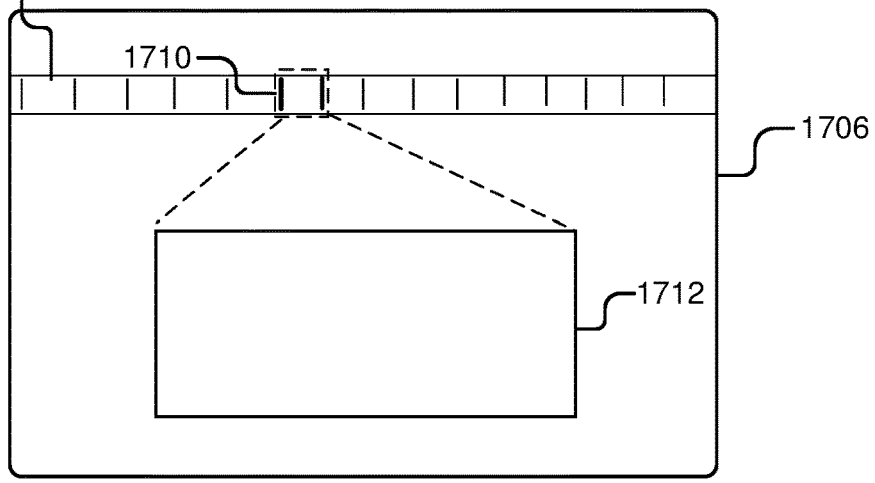

FIGS. 17A-17C are graphic representations of example interfaces for displaying photos/videos. In some implementations, the user interface module 506 may communicate with the photo widget 1508 and the video widget 1510 to generate the interfaces 1702-1706 to display the photo/video data associated with one or more health activities. FIG. 17A presents a mosaic display of the photos and/or videos in a print interface 1702. The interface 1702 is "print" because a user can only view the photos and videos without any control to the content and arrangement of the display.

FIG. 17B includes a browse&select interface 1704 that displays the videos/photos as slides in a row. In addition to viewing the photos/videos, a user may take action to rearrange the slides in the interface 1704. For example, a user may select a slide of the photo/video displayed on his smartphone, and drag and move the selected slide to a different position of the row for updating and display of the interface 1704. Similar to FIG. 17B, the user interface 1706 of FIG. 17C also allows users to have a certain level of control to the display of the photos/video. In FIG. 17C, the photos/videos are displayed according to the timeline 1708. When a user selects a health incident occurred at the time interval 1710, the corresponding photos/videos will be identified and displayed in the area of 1712.

In some implementations, the photo widget 1508 and/or the video widget 1510 allows an authorized user to connect to a photo/video cloud (e.g., a Facebook photobook) to select and retrieve a photo/video via the interfaces in FIGS. 17B and 17C. A user may be authorized to access and retrieve data from the photo/video cloud based on the PHICU access control in the blockchain health cloud 104. The user may then add or create his/her photo cloud based on the selected photo/video. As a result, the photo widget 1508 and/or the video widget 1510 may communicate with the user interface module 506 to update the interfaces of FIGS. 17B and 17C to display the selected photo/video.

Figure 18A:
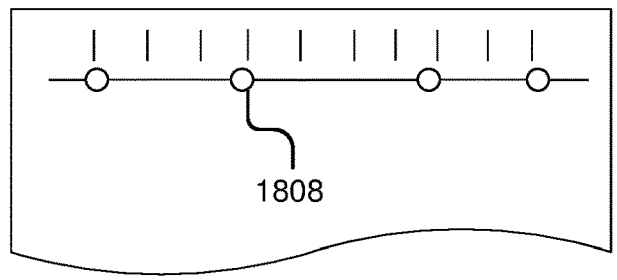
FIGS. 18A-18C are graphic representations of example interfaces for displaying timelines in accordance with the present disclosure.
Figure 18B:
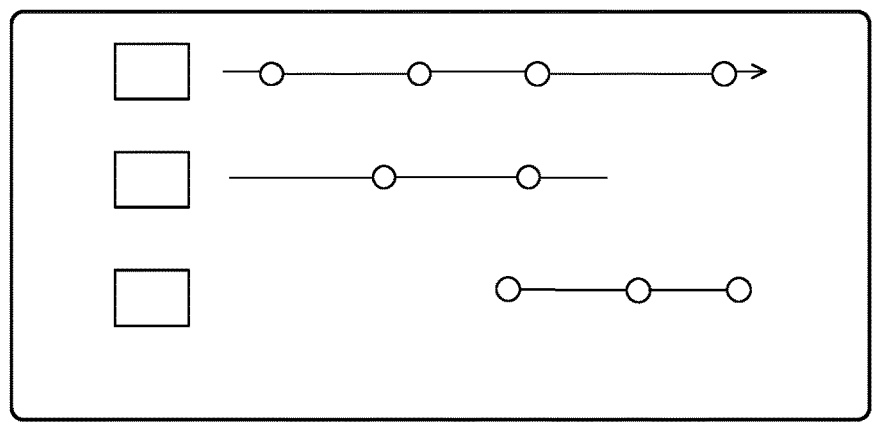
Figure 18C:
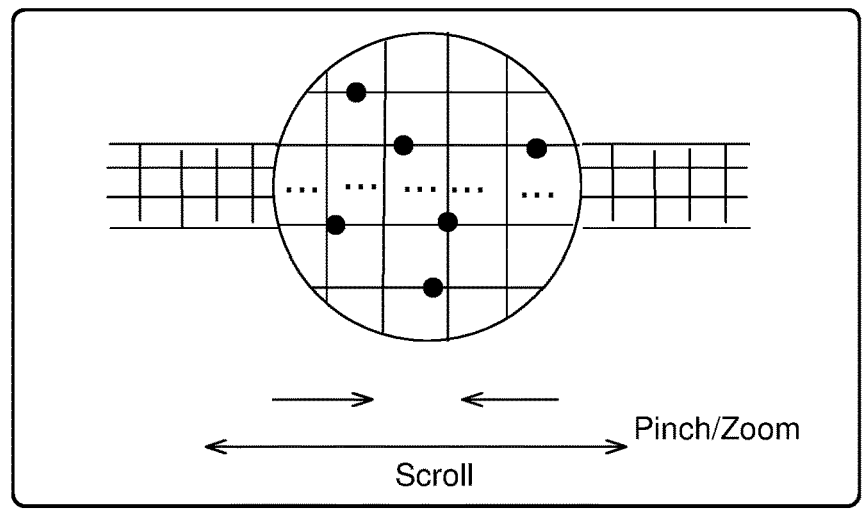

FIGS. 18A-18C are graphic representations of example interfaces for displaying timelines. In some implementations, the user interface module 506 may communicate with timeline widget(s) 1504 to generate the interfaces 1802-1806 to display timelines associated with one or more health activities. FIG. 18A shows a paper widget display 1802 of a timeline. A user may only view the timeline in the paper widget display. In some implementations, the timeline widget 1504 may generate a timeline to represent a relevant health activity/incident associated with a the patient. In other implementations, the timeline widget 1504 may identify multiple health activities associated with the patient, and combine them together in an order to form a single timeline. In a practical application, the timeline widget 1504 may change at least one of the size, shape or color of the points 1808 to represent a health incident's associated datapoint quality, which visually and intuitively exposes those qualities and therefore improves the user experience and system performance.

FIG. 18B shows a low density display 1804 of multiple timelines. A rectangular box on the left of each timeline may describe the timeline, e.g., Rx timeline. Each sphere or round point of the timeline represents a health incident data point. In some implementations, the timeline widget 1504 allows a user to operate on the low density display 1804 to create or modify a timeline. For example, responsive to receiving a user's click/tap on one of the multiple timelines, the timeline widget 1504 in communication with the user interface module 506 generates a new edit window to accept the user's input about date/time and data. As a result, the timeline widget 1504 instructs the user interface module 506 to add a new point to the timeline to represent a new data point for that health activity.

FIG. 18C shows a high density display 1806 of multiple timelines. As compared to the low density display 1804, the timeline widget 1504 in communication with the user interface module 506 generates the high density display 1806 to display more health activities that occurred in a longer timeline. A user may scroll the timeline to view the health activities and their data points that occurred within different time periods of the entire time of the patient. The user may also pinch the screen of a hardware device (e.g., a smart watch) that shows the high density display 1806 to zoom in the timeline such that the user can choose a specific health activity data point for view from the magnified timeline.

Figure 19B:
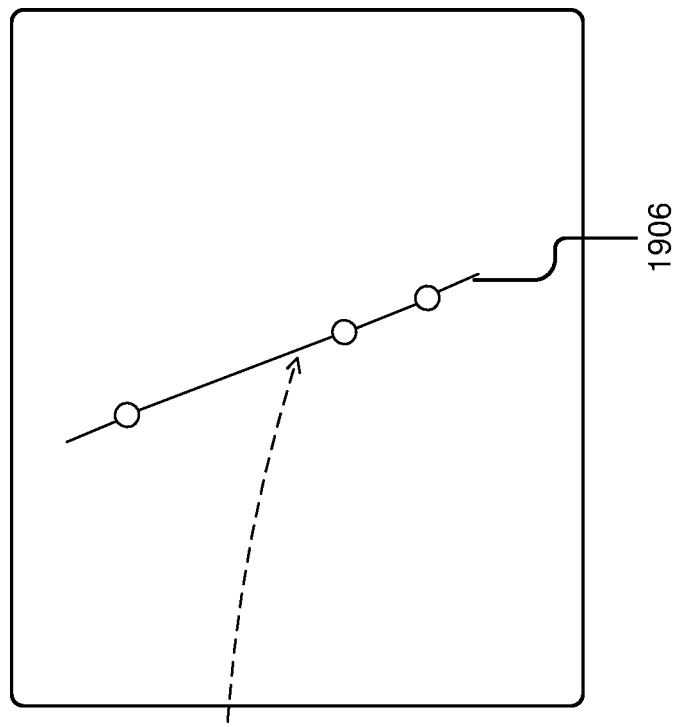
FIGS. 19A and 19B are graphic representations of an example interface for displaying timelines in three dimensions in accordance with the present disclosure.
Figure 19A:
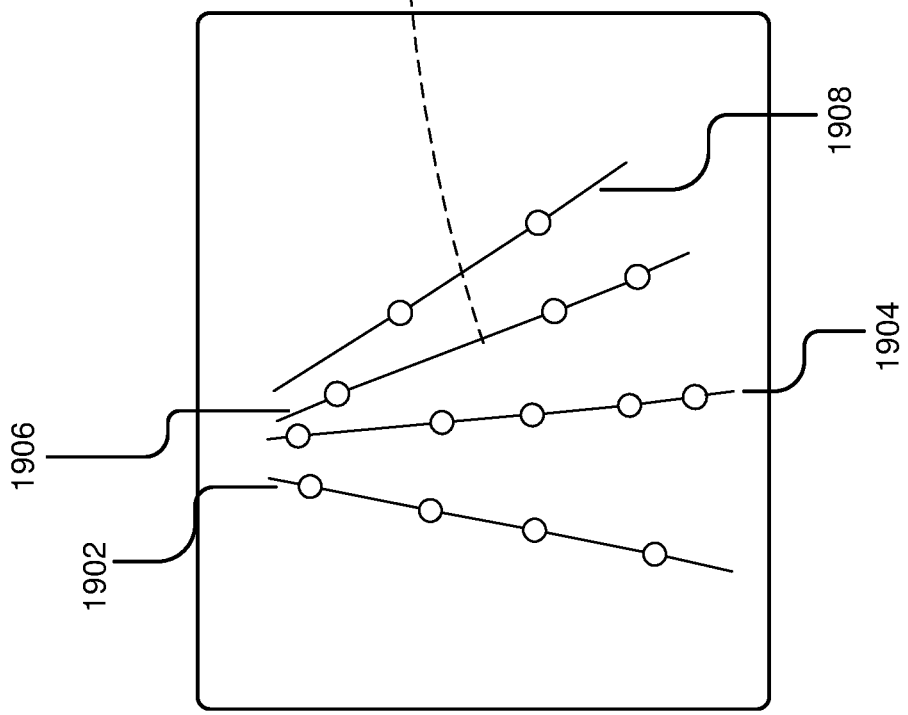

FIGS. 19A and 19B are graphic representations of example interfaces for displaying timelines in three-dimension. The timeline widget 1504 instructs the user interface module 506 to display four timelines 1902-1908 on a three-dimensional user interface of FIG. 19A. The health XR applications 814 or health AR applications 816 along with a hardware device supporting the XR and/or AR features allows a user to view or operate on the timelines 1902-1908. For example, the timeline widget 1504 may take user's hand gesture, eye movement to change the view of the timelines or modify the timelines. As the user pulls out a timeline for inspection, responsively the timeline widget 1504 may instruct the user interface tool 506 to generate an updated user interface as shown in FIG. 19B to display only the timeline 1906 to the user with more detail and controls than in FIG. 19A.

Some implementations may be described using the expression "one implementation" or "an implementation" along with their derivatives. These terms mean that a particular feature, structure, or characteristic described in connection with the implementation is included in at least one implementation. The appearances of the phrase "In some implementations" in various places in the specification are not necessarily all referring to the same implementation. Further, some implementations may be described using the expression "coupled" and "connected" along with their derivatives. These terms are not necessarily intended as synonyms for each other. For example, some implementations may be described using the terms "connected" and/or "coupled" to indicate that two or more elements are in direct physical or electrical contact with each other. The term "coupled," however, may also mean that two or more elements are not in direct contact with each other, but yet still co-operate or interact with each other. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single implementation for the purpose of streamlining the disclosure. This method of disclosure is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separate implementation. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but it should be understood that many further combinations and permutations are possible. Accordingly, the novel architecture is intended to embrace all such alterations, modifications and variations that fall within the spirit and scope of the appended claims.

As used herein, an element or step recited in the singular and proceeded with the word "a" or "an" should be understood as not excluding plural elements or steps, unless such exclusion is explicitly recited. Furthermore, references to "one implementation" of the present invention are not intended to be interpreted as excluding the existence of additional implementations that also incorporate the recited features.

While certain implementations of the disclosure have been described herein, it is not intended that the disclosure be limited thereto, as it is intended that the disclosure be as broad in scope as the art will allow and that the specification be read likewise. Therefore, the above description should not be construed as limiting, but merely as exemplifications of particular implementations. It should be understood that other modifications are within the scope and spirit of the claims appended hereto.

What is claimed is:

1. A computer-implemented method comprising:
    detecting, by a health activity unit, a health activity of a user, wherein the health activity is based on a user interaction related to a healthcare need and a hardware device of the user;
    sending, responsive to detecting the health activity of the user, a request for a first protected health information address to a blockchain health cloud;
    receiving the first protected health information address for the user;
    identifying health data associated with the health activity, wherein the identified health data comprises protected health information;
    identifying a task to be performed based on the health activity and the identified health data, wherein the task comprises adding the identified health data to a health data blockchain associated with the health activity;
    determining, based on a first data block of the health data blockchain, whether the user is an authorized user of the identified health data;
    responsive to the user being authorized, determining a health activity state from a second data block of the health data blockchain;
    updating the health activity state from the second data block;
    creating, based on updating the health activity state from the second data block, a third data block to add the identified health data to the health data blockchain, wherein the third data block comprises a smart contract in blockchain code of the third data block for controlling access to the identified health data;
    sending the third data block to the blockchain health cloud;
    receiving, responsive to sending the third data block to the blockchain health cloud, a contract address for the identified health data;
    locking data access to the identified health data using the contract address; and propagating and validating the third data block across a plurality of protected health information control units, wherein:
the health activity unit comprises the plurality of protected health information control units; and
each protected health information control unit of the plurality of protected health information control units is:
associated with a different hardware device associated with a patient; and
configured to control access to the identified health data from that different hardware device.

2. The computer-implemented method of claim 1, wherein:
the health activity unit comprises a plurality of interface modules for a plurality of hardware devices associated with the patient;
the plurality of interface modules includes an interface module for the hardware device of the user;
each interface module of the plurality of interface modules comprises:
a hardware device interface for that different hardware device associated with the patient; and
the protected health information control unit from the plurality of protected health information control units for at least one user of that different hardware device;
determining whether the user is an authorized user of the identified health data is further based on the protected health information control unit associated with the hardware device of the user; and
each protected health information control unit includes at least one data block of a plurality of data blocks in the health data blockchain.

3. The computer-implemented method of claim 2, further comprising:
generating, based on the plurality of interface modules, a user interface for the plurality of hardware devices of a plurality of users with a unified view of the updated health activity state associated with the health activity.

4. The computer-implemented method of claim 3, wherein generating the user interface includes displaying one or more health activities on one or more timelines in different views.

5. The computer-implemented method of claim 2, further comprising:
storing the second data block in a health activity controller of the health activity unit; and
storing the first data block in the protected health information control unit associated with the user and the hardware device of the user.

6. The computer-implemented method of claim 1, further comprising:
receiving a second protected health information address for a delegate of the user;
creating, based on the second protected health information address, a fourth data block;
sending the fourth data block to the blockchain health cloud;
receiving a contract address for the fourth data block; and
configuring delegate access rights for the delegate of the user at the contract address for the fourth data block.

7. The computer-implemented method of claim 1, wherein the identified health data is stored and retrieved from one or more internal domains of a healthcare entity and one or more outside domains of the healthcare entity.

8. The computer-implemented method of claim 1, wherein:
detecting the health activity comprises receiving an input regarding the health activity from the hardware device of the user; and
identifying the health data associated with the health activity is based on the input.

9. The computer-implemented method of claim 1, further comprising tracking and monitoring one or more health activities and associated health data.

10. A system, comprising:
a processor;
a memory;
a health activity unit, stored in the memory for execution by the processor, comprising instructions for:
detecting a health activity of a user, wherein the health activity is based on a user interaction related to a healthcare need and a hardware device of the user;
sending, responsive to detecting the health activity of the user, a request for a first protected health information address to a blockchain health cloud;
receiving the first protected health information address for the user;
identifying health data associated with the health activity, wherein the identified health data comprises protected health information;
identifying a task to be performed based on the health activity and the identified health data, wherein the task comprises adding the identified health data to a health data blockchain associated with the health activity;
determining, based on a first data block of the health data blockchain, whether the user is an authorized user of the identified health data;
responsive to the user being authorized, determining a health activity state from a second data block of the health data blockchain;
updating the health activity state from the second data block;
creating, based on updating the health activity state from the second data block, a third data block to add the identified health data to the health data blockchain, wherein the third data block comprises a smart contract in blockchain code of the third data block for controlling access to the identified health data;
sending the third data block to the blockchain health cloud;
receiving, responsive to sending the third data block to the blockchain health cloud, a contract address for the health data;
locking data access to the identified health data using the contract address; and
propagating and validating the third data block across a plurality of protected health information control units, wherein:
the health activity unit comprises the plurality of protected health information control units; and
each protected health information control unit of the plurality of protected health information control units is:
associated with a different hardware device associated with a patient; and
configured to control access to the identified health data from that different hardware device.

11. The system of claim 10, wherein:
the health activity unit comprises a plurality of interface modules for a plurality of hardware devices associated with the patient;
the plurality of interface modules includes an interface module for the hardware device of the user;
each interface module of the plurality of interface modules comprises:
a hardware device interface for that different hardware device associated with the patient; and
the protected health information control unit from the plurality of protected health information control units for at least one user of that different hardware device;
determining whether the user is an authorized user of the identified health data is further based on the protected health information control unit associated with the hardware device of the user; and
each protected health information control unit includes at least one data block of a plurality of data blocks in the health data blockchain.

12. The system of claim 11, wherein the health activity unit further comprises instructions for:
generating, based on the plurality of interface modules, a user interface for the plurality of hardware devices of a plurality of users with a unified view of the updated health activity state associated with the health activity.

13. The system of claim 12, wherein generating the user interface comprises displaying one or more health activities on one or more timelines in different views.

14. The system of claim 11, wherein the health activity unit further comprises instructions for:
storing the second data block in a health activity controller of the health activity unit; and
storing the first data block in the protected health information control unit associated with the user and the hardware device of the user.

15. The system of claim 10, wherein the health activity unit further comprises instructions for:
receiving a second protected health information address for a delegate of the user;
creating, based on the second protected health information address, a fourth data block;
sending the fourth data block to the blockchain health cloud;
receiving a contract address for the fourth data block; and
configuring delegate access rights for the delegate of the user at the contract address for the fourth data block.

16. The system of claim 10, wherein:
the identified health data is stored and retrieved from one or more internal domains of a healthcare entity and one or more outside domains of the healthcare entity.

17. The system of claim 10, wherein:
detecting the health activity comprises receiving an input regarding the health activity from the hardware device of the user; and
identifying the health data associated with the health activity is based on the input.

18. A non-volatile computer-readable storage medium, comprising instructions for:
detecting a health activity of a user, wherein the health activity is based on a user interaction related to a healthcare need and a hardware device of the user;
sending, responsive to detecting the health activity of the user, a request for a first protected health information address to a blockchain health cloud;
receiving the first protected health information address for the user;
identifying health data associated with the health activity, wherein the identified health data comprises protected health information;
identifying a task to be performed based on the health activity and the identified health data, wherein the task comprises adding the identified health data to a health data blockchain associated with the health activity;
determining, based on a first data block of the health data blockchain, whether the user is an authorized user of the identified health data;
responsive to the user being authorized, determining a health activity state from a second data block of the health data blockchain;
updating the health activity state from the second data block;
creating, based on updating the health activity state from the second data block, a third data block to add the identified health data to the health data blockchain, wherein the third data block comprises a smart contract in blockchain code of the third data block for controlling access to the identified health data;
sending the third data block to the blockchain health cloud;
receiving, responsive to sending the third data block to the blockchain health cloud, a contract address for the health data;
locking data access to the identified health data using the contract address; and
propagating and validating the third data block across a plurality of protected health information control units, wherein:
a health activity unit comprises the plurality of protected health information control units; and
each protected health information control unit of the plurality of protected health information control units is:
associated with a different hardware device associated with a patient; and
configured to control access to the identified health data from that different hardware device.

* * * * *